(12) United States Patent
Satovsky et al.

(10) Patent No.: US 12,220,255 B2
(45) Date of Patent: Feb. 11, 2025

(54) VESSEL LOCATION ASSISTANCE DEVICE

(71) Applicant: NOVOTEC LLC, Boca Raton, FL (US)

(72) Inventors: James B. Satovsky, Boca Raton, FL (US); Farhad Bybordi, Delray Beach, FL (US); Steven M. Lurcott, Deerfield Beach, FL (US)

(73) Assignee: NOVOTEC LLC

( * ) Notice: Subject to any disclaimer, the term of this patent is extended or adjusted under 35 U.S.C. 154(b) by 40 days.

(21) Appl. No.: 17/349,804

(22) Filed: Jun. 16, 2021

(65) Prior Publication Data

US 2022/0031232 A1 Feb. 3, 2022

Related U.S. Application Data

(60) Provisional application No. 63/058,553, filed on Jul. 30, 2020.

(51) Int. Cl.
*A61B 5/00* (2006.01)
*G01N 21/47* (2006.01)

(52) U.S. Cl.
CPC ............ *A61B 5/489* (2013.01); *A61B 5/0062* (2013.01); *A61B 5/0075* (2013.01); *G01N 21/4738* (2013.01); *G01N 2021/4709* (2013.01)

(58) Field of Classification Search
CPC ..... A61B 5/489; A61B 5/0062; A61B 5/0075; A61B 5/0082; G01N 21/4738; G01N 2021/4709

See application file for complete search history.

(56) References Cited

U.S. PATENT DOCUMENTS

| | | | |
|---|---|---|---|
| 308,908 | A | 12/1884 | Lighthill |
| 3,171,410 | A | 3/1965 | Towle, Jr. et al. |
| 3,620,209 | A | 11/1971 | Kravitz |
| 3,745,989 | A | 7/1973 | Pinna |
| 3,998,210 | A | 12/1976 | Nosari |
| D259,210 | S | 5/1981 | Ayer |
| 4,667,679 | A | 5/1987 | Sahota |
| 4,817,622 | A | 4/1989 | Pennypacker et al. |
| 4,834,802 | A | 5/1989 | Prier |

(Continued)

FOREIGN PATENT DOCUMENTS

| | | |
|---|---|---|
| CA | 2635851 A1 | 7/2007 |
| CN | 1439433 A | 9/2003 |

(Continued)

OTHER PUBLICATIONS

International Search Report, PCT/EP2015/074578, Jan. 28, 2016.

(Continued)

*Primary Examiner* — Christopher L Cook
(74) *Attorney, Agent, or Firm* — Charney IP Law LLC

(57) ABSTRACT

A vessel location assistance device having a housing with a proximal portion and a distal portion, an infrared light emitter adapted to emit infrared light from the housing to a patient and an infrared light receiver adapted to receive backscattered infrared light intensity reflected from the patient, wherein the received backscattered infrared light intensity is converted to a voltage and when the voltage is within a calibrated range the device indicates the presence of a blood vessel. The device may further include at least one wing with a slot for capturing the blood vessel.

29 Claims, 25 Drawing Sheets

(56) References Cited

U.S. PATENT DOCUMENTS

| | | | |
|---|---|---|---|
| 5,167,629 A | 12/1992 | Vertenstein et al. | |
| 5,263,966 A | 11/1993 | Daneshvar | |
| 5,300,086 A | 4/1994 | Gory et al. | |
| 5,309,915 A | 5/1994 | Ember | |
| 5,678,555 A | 10/1997 | O'Connell | |
| 5,749,371 A | 5/1998 | Zadini et al. | |
| 5,749,853 A | 5/1998 | O'Donnell | |
| 5,749,856 A | 5/1998 | Zadini et al. | |
| 6,463,309 B1 | 10/2002 | Ilia | |
| 6,672,312 B2 | 1/2004 | Acker | |
| D492,776 S | 7/2004 | Nilsson | |
| 7,253,014 B2 | 8/2007 | Barron et al. | |
| D559,979 S | 1/2008 | Suematsu | |
| 7,874,698 B2 | 1/2011 | Mullani | |
| 7,904,138 B2 | 3/2011 | Goldman et al. | |
| 7,983,738 B2 | 7/2011 | Goldman et al. | |
| 8,078,261 B2 | 12/2011 | Imam | |
| 8,150,500 B2 | 4/2012 | Goldman et al. | |
| 8,255,040 B2 | 8/2012 | Goldman et al. | |
| 8,380,291 B2 | 2/2013 | Wood et al. | |
| 8,388,579 B2 | 3/2013 | Rutkowski | |
| 8,463,364 B2 | 6/2013 | Wood et al. | |
| 8,498,694 B2 | 7/2013 | McGuire, Jr. et al. | |
| 8,706,200 B2* | 4/2014 | Goldman | A61B 5/7221 600/407 |
| 8,712,498 B2 | 4/2014 | Goldman et al. | |
| 8,750,970 B2 | 6/2014 | Goldman et al. | |
| 9,430,819 B2 | 8/2016 | Luciano et al. | |
| 9,522,240 B2 | 12/2016 | Lee et al. | |
| 9,974,630 B2* | 5/2018 | Heacock | A61C 1/0046 |
| D995,329 S | 8/2023 | Satovsky | |
| 11,751,758 B2 | 9/2023 | Lin | |
| 2005/0168980 A1 | 8/2005 | Dryden et al. | |
| 2005/0257795 A1 | 11/2005 | Hsiu-Chen et al. | |
| 2006/0020212 A1 | 1/2006 | Xu et al. | |
| 2006/0079792 A1 | 4/2006 | Finburgh | |
| 2007/0005045 A1* | 1/2007 | Mintz | A61B 34/30 606/1 |
| 2007/0088346 A1 | 4/2007 | MirizZi et al. | |
| 2007/0161909 A1 | 7/2007 | Goldman et al. | |
| 2008/0027317 A1 | 1/2008 | Wood et al. | |
| 2008/0147147 A1* | 6/2008 | Griffiths | A61B 5/489 600/461 |
| 2009/0105594 A1 | 4/2009 | Reynolds et al. | |
| 2009/0234261 A1 | 9/2009 | Singh | |
| 2010/0177182 A1 | 7/2010 | Kagenow et al. | |
| 2010/0331709 A1 | 12/2010 | Matsumura et al. | |
| 2010/0331712 A1 | 12/2010 | Rothenberg | |
| 2011/0021925 A1 | 1/2011 | Wood et al. | |
| 2011/0202003 A1 | 8/2011 | Cook | |
| 2011/0313294 A1 | 12/2011 | de Roode et al. | |
| 2012/0029494 A1 | 2/2012 | Wittenberger et al. | |
| 2013/0102905 A1 | 4/2013 | Goldman et al. | |
| 2013/0317373 A1* | 11/2013 | Warren | A61B 5/683 600/479 |
| 2014/0024952 A1 | 1/2014 | Wood et al. | |
| 2014/0114117 A1 | 4/2014 | Naghavi et al. | |
| 2014/0155753 A1* | 6/2014 | McGuire, Jr. | A61B 5/6833 600/476 |
| 2015/0025402 A1 | 1/2015 | Rothenberg | |
| 2015/0119802 A1 | 4/2015 | Dumitrescu | |
| 2016/0135733 A1 | 5/2016 | Wood et al. | |
| 2017/0105665 A1* | 4/2017 | Ravikumar | A61B 5/15074 |
| 2017/0156665 A1 | 6/2017 | Miller et al. | |
| 2017/0325825 A1 | 11/2017 | Bybordi | |
| 2019/0076070 A1 | 3/2019 | Nogueira et al. | |
| 2019/0200866 A1* | 7/2019 | Eom | A61B 5/02007 |
| 2020/0201657 A1* | 6/2020 | Kang | G16B 20/00 |

FOREIGN PATENT DOCUMENTS

| | | | |
|---|---|---|---|
| CN | 101791249 A | 8/2010 | |
| CN | 202342051 U | 7/2012 | |
| CN | 205597900 U | 9/2016 | |
| CN | 111419184 | 1/2023 | |
| CN | 111419184 B | 1/2023 | |
| DE | 102007025132 A1 | 4/2013 | |
| EP | 0601756 B1 | 9/1998 | |
| EP | 2124728 A2 | 12/2009 | |
| EP | 1981395 B1 | 6/2013 | |
| FR | 2204388 A1 | 5/1974 | |
| JP | H02172473 A | 7/1990 | |
| JP | 2006102029 A | 4/2006 | |
| WO | 1998046144 A1 | 10/1998 | |
| WO | 2006014868 A2 | 2/2006 | |
| WO | 2008094253 A2 | 8/2008 | |
| WO | WO-2009037432 A1 * | 3/2009 | ........... A61B 5/0059 |
| WO | 2010029521 A2 | 3/2010 | |
| WO | 2011116347 A1 | 9/2011 | |
| WO | 2012011951 A1 | 1/2012 | |
| WO | WO-2012063229 A2 * | 5/2012 | ........... A61B 5/0059 |
| WO | 2015054321 A1 | 4/2015 | |
| WO | 2017056870 A1 | 4/2017 | |

OTHER PUBLICATIONS

Veinfinder array resulting from internet search, dated no later than Jun. 14, 2021.

International Preliminary Report on Patentability, PCT/GB2008/003132, Mar. 24, 2010.

Written Opinion of the International Searching Authority, PCT/EP2015/074578, undated.

* cited by examiner

| Test | ADC Response (bits) | | | | | | ADC Response (volts) | | |
|---|---|---|---|---|---|---|---|---|---|
| | Hex(1) | hex(2) | Hex(3) | Decimal(1) | Decimal(2) | Decimal(3) | Vdet(1) | Vdet(2) | Vdet(3) |
| open air | 50 | 5d | 62 | 80 | 93 | 98 | 0.2578125 | 0.299702031 | 0.315820313 |
| vein | 100 | d8 | 121 | 256 | 216 | 289 | 0.825 | 0.696009375 | 0.931347656 |
| no vein | 120 | 1b1 | 1bc | 288 | 433 | 444 | 0.928125 | 1.395431156 | 1.430859375 |
| threshold | | | | 200 | 200 | 200 | 0.64453125 | 0.64453125 | 0.64453125 |
| vein | 191 | f9 | 15c | 401 | 249 | 348 | 1.292285156 | 0.802441406 | 1.121484375 |
| no vein | 108 | 161 | 176 | 264 | 353 | 374 | 0.850781125 | 1.137597656 | 1.205273438 |
| floor | 50 | 5d | 69 | 80 | 93 | 105 | 0.2578125 | 0.299707031 | 0.338378906 |
| cieling | 50 | 5f | 5f | 80 | 95 | 95 | 0.2578125 | 0.306152344 | 0.306152344 |
| 6" from skin | 50 | 5a | 59 | 80 | 90 | 89 | 0.2578125 | 0.290038063 | 0.286816406 |
| 1" from skin | 60 | 6e | 72 | 96 | 110 | 114 | 0.309375 | 0.354492188 | 0.367382813 |

0.003222656 volts/bit

FIGURE 2

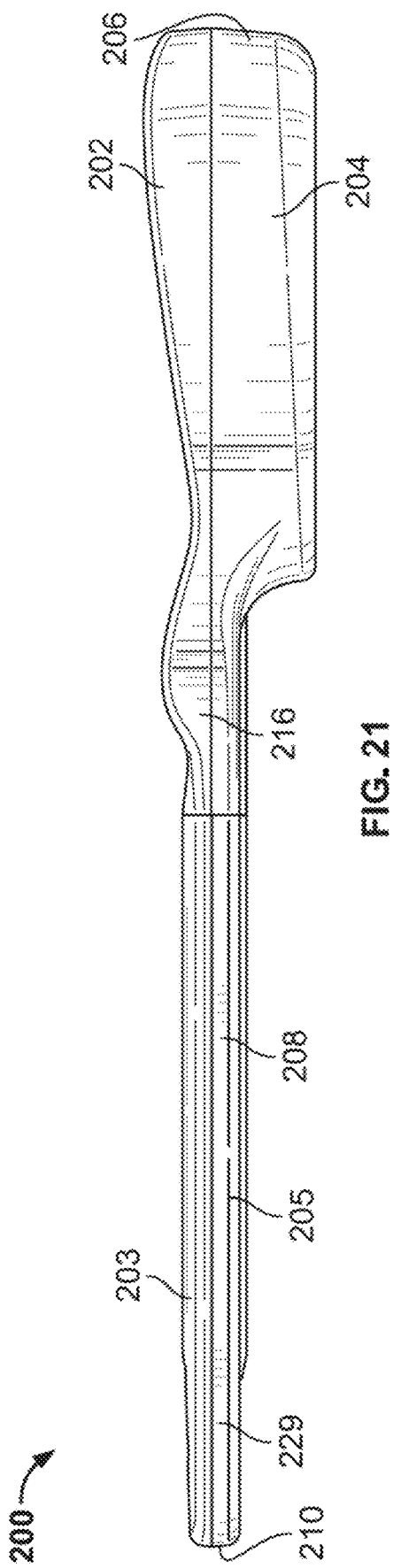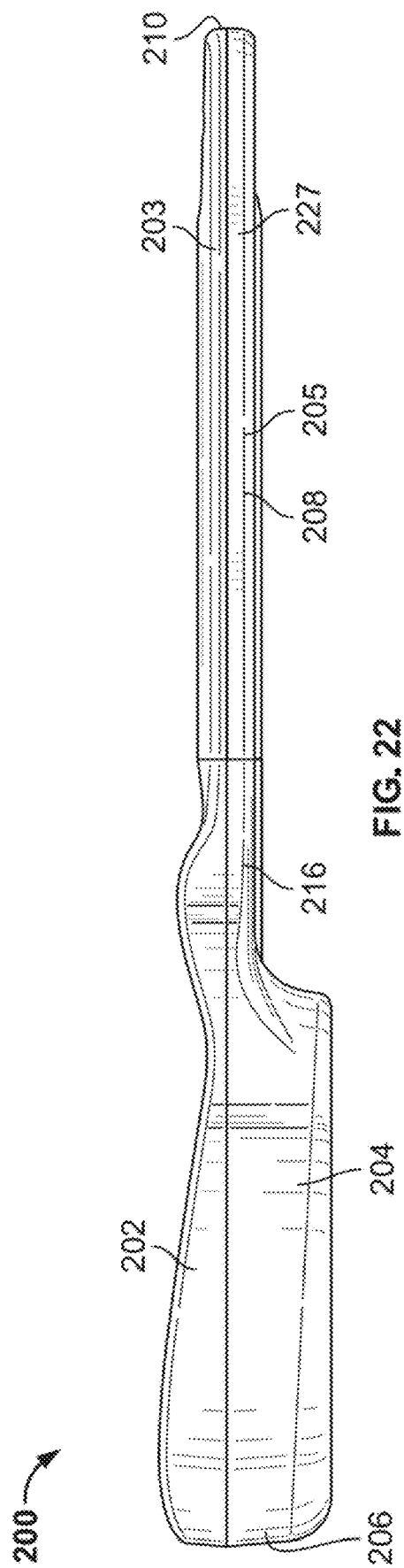

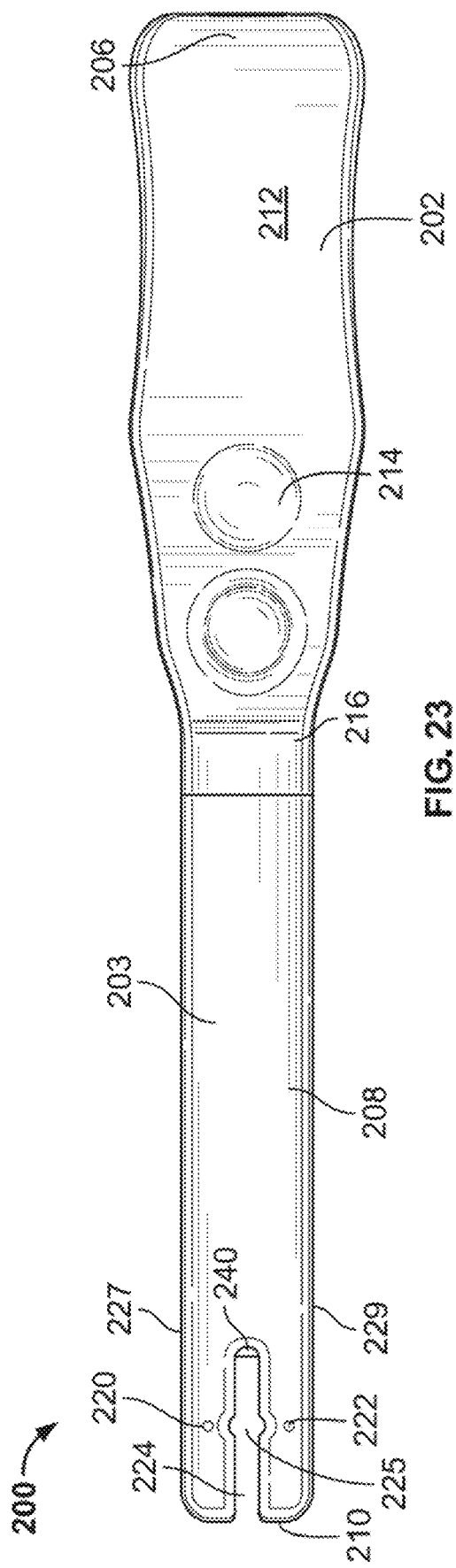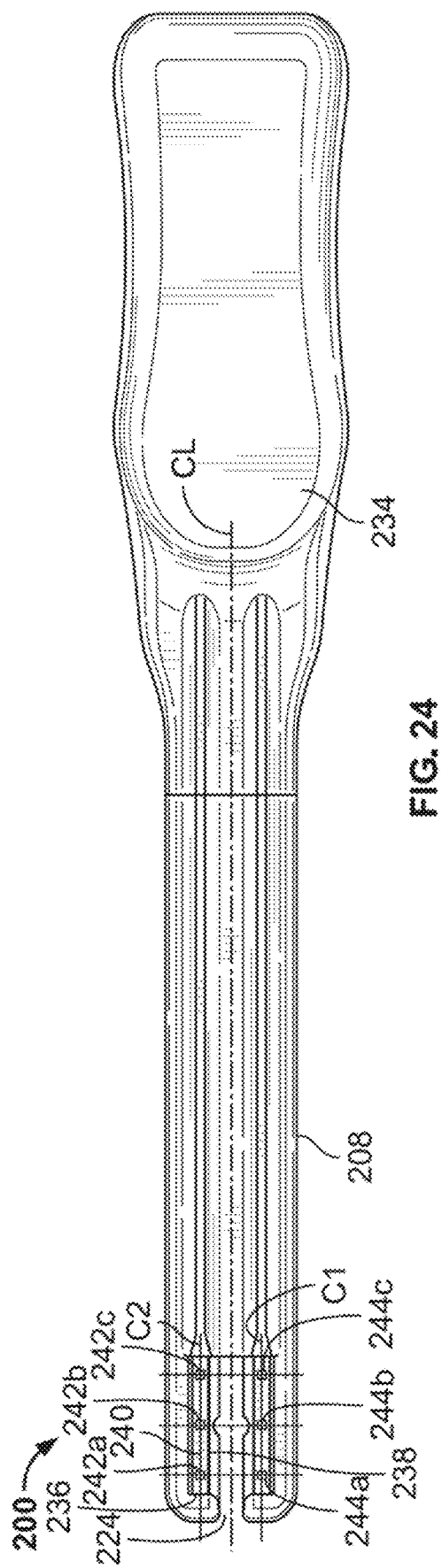
FIG. 23
FIG. 24

VESSEL LOCATION ASSISTANCE DEVICE

CROSS-REFERENCE TO RELATED APPLICATIONS

The present application claims the benefit of U.S. Provisional Application Ser. No. 63/058,553 entitled "Blood Vessel and Mandibular Nerve Detector Devices," filed Jul. 30, 2020, the disclosures of which are hereby incorporated by reference herein.

BACKGROUND OF THE INVENTION

The present invention relates to devices and methods for locating blood vessels within a mammalian body using infrared technology. It is well known that infrared radiation is reflected from general mammalian tissue yet, conversely, is absorbed by blood vessels. Thus, one may administer infrared radiation to the skin in a controlled manner and analyze the patterns of returned and back scattered signals to identify the precise location of a blood vessel.

Literature on this technology can be found as early as World Intellectual Property Publication No. WO/2009/037432 by Bybordi, an inventor herein.

BRIEF SUMMARY OF THE INVENTION

Despite the earlier technologies, there have been found improvements and additional features enabling this technology to be more suitable for widespread use and commercialization.

Provided herein are multiple embodiments of a VESSEL LOCATION ASSISTANCE DEVICE in accordance with the present invention. In one embodiment, the VESSEL LOCATION ASSISTANCE DEVICE may include a vessel location assistance device having a housing with a proximal portion and a distal portion, the proximal portion and the distal portion spaced apart along a centerline of the housing, the housing having a top portion and a bottom portion; an aperture positioned in the distal portion along the centerline, the aperture penetrating through the top portion and the bottom portion of the housing; at least one light associated with the housing; three infrared light emitters adapted to emit infrared light from the bottom portion of the housing to a patient and three infrared light receivers adapted to receive backscattered infrared light reflected from the patient; the three infrared light emitters and the three infrared light receivers arranged in pairs along equally spaced rows, including a middle row and two remaining rows, each equally spaced row extending perpendicular to the centerline, wherein the middle row of the three rows is aligned with the aperture; the three emitters and three receivers arranged in two columns extending along axes equally spaced and parallel to the centerline; wherein each pair of the three emitters and three receives is serially and repeatedly energized to emit infrared light and detect backscattered infrared light intensity from the patient when the housing is positioned on or near a patient's skin, each of the detection intensities being converted to a voltage; and wherein, when a voltage of the middle row is less than a voltage of each of the two remaining rows the at least one light illuminates to indicate the presence of a patient's blood vessel nearest the middle row of the three rows.

The infrared light emitters may be arranged along a single column.

The light may be a pair of lights aligned with the middle row of the three rows.

The vessel location assistance device may include a pair of wings, each having a slot extending perpendicular to the centerline and along an axis of the middle row.

The proximal portion and the distal portion of the housing may be separable.

Where the proximal portion and the distal portion of the housing are separable, the distal portion may be sized and configured to fit within a patient's mouth such that the middle row can reach at least to the inferior alveolar nerve adjacent to and on the medial side of the ramus of the mandible.

Where the proximal portion and the distal portion of the housing are separable, the vessel location assistance device may include a central processing unit and a battery, the central processing unit and the battery being located within the proximal portion of the device.

Where the proximal portion and the distal portion of the housing are separable, and the vessel location assistance device includes a central processing unit and a battery, the central processing unit and the battery being located within the proximal portion of the device, the three infrared light emitters and the three infrared light receivers may be located within the distal portion of the device.

The light may be a blue LED light.

The light may be a red LED light.

The three infrared light receivers may be spaced apart sufficiently to avoid crosstalk.

The aperture may be a circle, oval, rectangle, or slot sufficiently sized to permit penetration by a hypodermic needle.

The vessel location assistance device may further include a central processing unit, the central processing unit being programmable to adjust a divergence level between the voltage of the middle row and the voltage of each of the two remaining rows prior to the one light illuminating to indicate the presence of a patient's blood vessel nearest the middle row of the three rows.

A divergence level between the voltage of the middle row and the voltage of each of the two remaining rows may be user adjustable between at least two settings.

Where a divergence level between the voltage of the middle row and the voltage of each of the two remaining rows is user adjustable between at least two settings, the adjustments may account for differing skin characteristics.

Where a divergence level between the voltage of the middle row and the voltage of each of the two remaining rows is user adjustable between at least two settings, and the adjustments account for differing skin characteristics, the differing skin characteristics may be the amount of subcutaneous fatty tissue a patient has or skin tone.

A minimum level of backscattered infrared light may be required in all three infrared light receivers prior to the at least one light illuminating.

Each pair of the three emitters and three receivers may be serially and sequentially repeatedly energized at an adjustable rate.

Each pair of the three emitters and three receivers may be serially and repeatedly energized at a rate between 4 and 6 times per second.

The at least one light may include an intensity, wherein the intensity is adjustable.

In a further embodiment of the present invention, a vessel location assistance device may include a housing having a proximal portion and a distal portion, the proximal portion and the distal portion spaced apart along a centerline of the housing, the housing having a top portion and a bottom portion; three infrared light emitters adapted to emit infrared light from the bottom portion of the housing to a patient and three infrared light receivers adapted to receive backscattered infrared light reflected from the patient; the three infrared light emitters and the three infrared light receivers arranged in pairs along equally spaced rows, including a middle row and two remaining rows, each equally spaced row extending perpendicular to the centerline; the three emitters and three receivers arranged in two columns extending along axes equally spaced and parallel to the centerline; wherein each pair of the three emitters and three receives is serially and repeatedly energized to emit infrared light and detect backscattered infrared light intensity from the patient when the housing is positioned on or near a patient's skin, each of the detection intensities being converted to a voltage; and wherein, when a voltage of the middle row is less than a voltage of each of the two remaining rows the device indicates the presence of a patient's blood vessel nearest the middle row of the three rows.

The indication may be by visual or audial means.

In a still further embodiment of the present invention, a vessel location assistance device may include a housing having a proximal portion and a distal portion; an infrared light emitter adapted to emit infrared light from the housing to a patient and an infrared light receiver adapted to receive backscattered infrared light intensity reflected from the patient; wherein the received backscattered infrared light intensity is converted to a voltage; wherein, when the voltage is within a calibrated range the device indicates the presence of a blood vessel.

BRIEF DESCRIPTION OF THE DRAWINGS

The foregoing exemplary embodiments, as well as the following detailed description of the present disclosure, will be better understood when considered in view of the appended drawings. For the purposes of illustrating the present disclosure, there are shown in the drawings exemplary embodiments. It should be understood, however, that the present disclosure is not limited to the precise arrangements and instrumentalities shown and that other embodiments and modalities may also be effectively adapted and utilized.

In the drawings:

FIG. 2 depicts a table calibration test results for a device in various situations;

FIG. 21 depicts a left side view of the device of FIG. 18;

FIG. 22 depicts a right side view of the device of FIG. 18;

FIG. 23 depicts a top view of the device of FIG. 18;

FIG. 24 depicts a bottom view of the device of FIG. 18;

DETAILED DESCRIPTION

Figure 1:
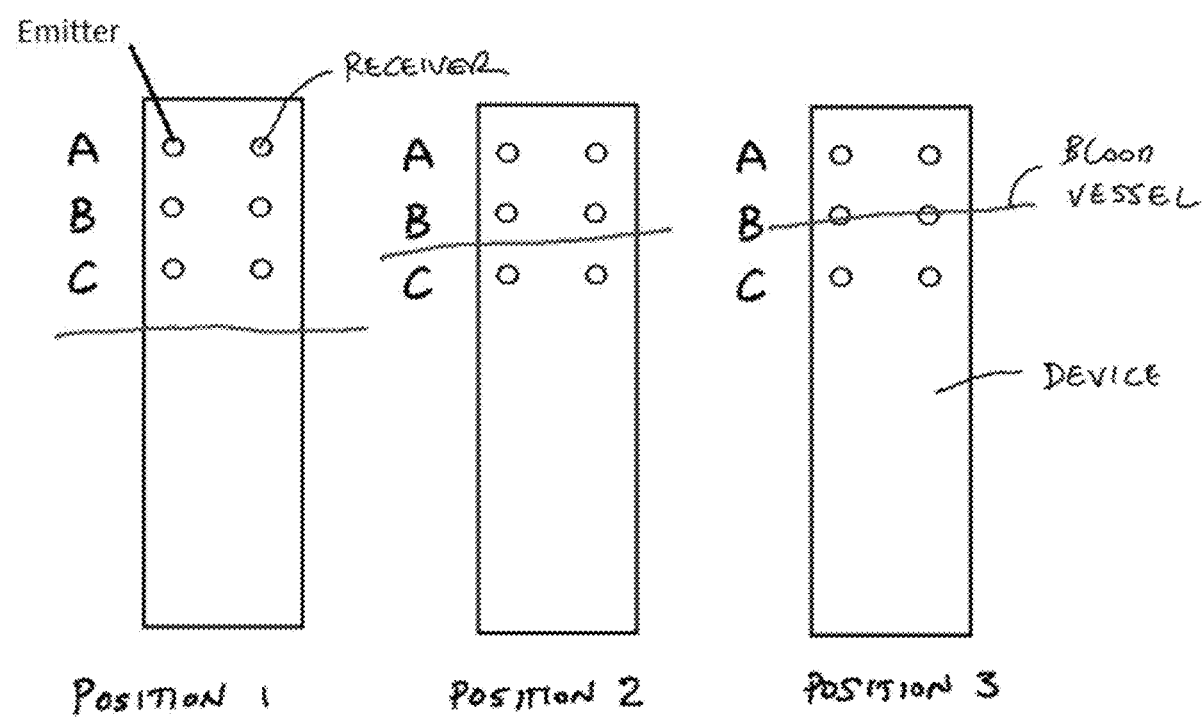
FIG. 1 depicts a sketch of the underside of a representative device located in three positions relative to a patient's blood vessel.

Reference will now be made in detail to the various aspects of the subject disclosure illustrated in the accompanying drawings. Wherever possible, the same or like reference numbers will be used throughout the drawings to refer to the same or like features. It should be noted that the drawings are in simplified form and are not drawn to precise scale.

In reference to the disclosure herein, for purposes of convenience and clarity only, directional terms such as top, bottom, left, right, above, below, and diagonal are used with respect to the accompanying drawings. Such directional terms used in conjunction with the following description of the drawings should not be construed to limit the scope of the subject disclosure in any manner not explicitly set forth.

Additionally, the term "a," as used in the specification, may be construed to mean "at least one." The terminology includes the words above specifically mentioned, derivatives thereof, and words of similar import.

The terms "about," "approximately," "generally," and the like as used herein when referring to a measurable value, such as an amount, a temporal duration, and the like, are meant to encompass variations such as ±20%, ±10%, ±5%, ±1%, or ±0.1% and the like from the specified value, as such variations are appropriate in the context of the disclosure and the art.

Throughout this disclosure, various aspects of the subject disclosure can be presented in a range format. It is to be understood that the description in range format is merely for convenience and brevity and should not be construed as an inflexible limitation on the scope of the subject disclosure. Accordingly, the description of a range should be considered to have specifically disclosed all the possible subranges as well as individual numerical values within that range. For example, description of a range, such as from 1 to 6, should be considered to have specifically disclosed subranges, such as from 1 to 3, from 1 to 4, from 1 to 5, from 2 to 4, from 2 to 6, from 3 to 6, from 2.5 to 4, from 2.7 to 3.2, from 5.1 to 5.5, etc., as well as individual numbers within that range, for example, 1, 2, 2.7, 3, 4, 5, 5.3, and 6. This applies regardless of the breadth of the range.

Furthermore, the described features, advantages, and characteristics of the subject disclosure may be combined in any suitable manner in one or more embodiments. One skilled in the relevant art will recognize, in light of the description herein, that the subject disclosure can be practiced without one or more of the specific features or advantages of a particular embodiment. In other instances, additional features and advantages may be recognized in certain embodiments that may not be present in all embodiments of the subject disclosure.

When used herein, the term "patient" shall refer to, without limitation, the person or animal that the device is being used on. Typically, that will be a medical or dental patient.

The term "caretaker" when used herein shall refer to, without limitation, the user of the devices. In most cases the caretaker will be a medical or dental professional, such as a doctor, dentist, or phlebotomist, but could also be a veterinarian or other user.

Caregivers are often required to find a blood vessel of a patient to administer intravenous injections, draw blood, or the like. The primary technique used today is visual observation. Visual observation works well for those patients with pronounced blood vessels or relatively light skin, but for those with dark skin, underlying fatty tissue, or abnormal skin masses, visual or even tactical means is insufficient.

As discussed, it is well known that infrared radiation is reflected from general mammalian tissue yet, conversely, is absorbed by blood vessels. Thus, one may administer infrared radiation to the skin of a patient in a controlled manner and subsequently record and analyze the patterns of returned and back scattered signals to identify the precise location of a blood vessel. Devices of the present invention may therefore be utilized in detecting the location of veins and arteries within a person or animal's body, without need for visual, tactical, or other observation or investigation. Similar infrared technology is commonly used in pulse oximeters and finger thumb vein pattern recognition for security devices.

Many blood vessels may be found using devices of the present invention. For example, one may effectively seek and find the median cephalic vein, median cubital vein, or the various veins of the hand's dorsal venous network blood draws, IV's, or other uses. The inventive devices may also be used for detecting the location of vessels before they enter the mandible intraorally for dental work. For purposes of simplification, it will be appreciated that this disclosure focuses on two separate devices, one for "medical" use and one for "dental" use.

Each of the devices utilizes the similar infrared technology, albeit calibrated for the particular use. Arrangements of exemplary devices will be discussed hereinafter. Each includes an underside with paired sensors arranged in three groups as will be discussed. Those paired sensors are preferably energized serially to detect backscattered infrared light emitted from one or more emitters.

With respect thereto, FIG. 1 depicts a sketch of the underside of a representative device located in three positions relative to a patient's blood vessel. On the underside are three emitters and three receivers grouped in three pairs, labelled Pair A, Pair B, and Pair C (it will be appreciated that the emitters may all be on the right as viewed in the image with the receivers on the left).

The emitter/receiver pairs are preferably all energized serially such that when infrared light is transmitted from an active emitter device backscatter is detected by the corresponding receiver. That is, Pair A is energized and the Pair A emitter emits an infrared signal, the Pair A receiver receives a backscatter signal, and the pair are deenergized. Pair B is then energized such that the Pair B emitter emits and infrared signal, the Pair B receiver receives a backscattered signal, and the pair is then deenergized. Finally, Pair C is energized, the Pair C emitter emits an infrared signal, the Pair B receiver receives a backscattered signal, and the Pair is deenergized. The process is then repeated.

Preferably, the refresh rate is in the range of ¼th of a second to 1/100th of a second. It has been found that flickering, i.e. too fast of a light refresh rate, occurs at the upper end of the range, but the lower end causes lag and less than ideal handling of the device. By way of example, refresh rates less than ¼th of a second cause the device to react too slowly. It has been found that caretakers can move the device too quickly for it to react, thus potentially bypassing a blood vessel during the interval where the device is not reactive. As such, a preferred range of between ⅕th and ⅙th of a second is generally found acceptable.

The backscattered signals are then analyzed by a central processing unit ("CPU") and a relative location of the device vis-à-vis a blood vessel is determined by way of a calibration threshold as will be discussed below. When the combined backscatter signal is within the calibrated threshold range, LED lights on the top side (not shown here and discussed below) are illuminated and a caretaker knows (s)he is directly above a blood vessel.

In this regard it will be appreciated that in Position 1, the receiver of Pair C will receive very little backscatter information as it is nearly adjacent to a blood vessel, which absorbs the infrared light. The receivers of Pairs A and B, hovering outside the limits of the blood vessel, will receive backscatter. In Position 2, backscatter on Pair C's receiver will still be influenced by the blood vessel while the receiver of Pair B will start to also be influenced. By Position 3, only the receiver of Pair B is truly influenced, and the CPU is calibrated to provide an indication that the user is directly over the blood vessel.

These readings can be calibrated by the CPU to be read individually, so that the indicator LED's on the topside of the device illuminate individually, or additively, such that the values of all three channels are added. In the latter instance, when the values are added it will be appreciated that the greatest backscatter signal received will be when the Pair B receiver receives a strong signal and the receivers of Pairs A and C each receive a smaller contribution.

In preferred embodiments the pairs are all read and then tested against a preconfigured threshold. That is, the voltage result of Pair A is read, the voltage result of Pair B is read, and then the voltage result of Pair C is read, sequentially. If one is properly over a vein, the voltage result of Pair B will be low relative to the voltage results of Pairs A and C, which will roughly be equal. This is because Pair B is over a blood vessel which absorbs more of the infrared light than does the skin. This will be discussed more fully as a "V" shaped response in relation to FIG. 3.

These sequential readings of pairs aids greatly in the avoidance of crosstalk between signals of adjacent pairs. Thus, a receiver from one pair will not read signals emitted from the emitter of a different pair. In some embodiments the pairs may be sufficiently spaced such that they may all be energized simultaneously and still avoid crosstalk. Generally speaking, and depending on the exact emitters and receivers used, there is a minimum distance that must be maintained between elements to avoid all crosstalk, even when the pairs are serially energized.

As the detected backscatter results in increased voltage readings, a table can be created from the test results. Shown in FIG. 2 is a table indicating calibration testing of a device in various situations, in accordance with one embodiment of the invention.

It will be appreciated that the response voltage is proportional to the level of backscatter signal received. That is, when a device is held in a position where no backscatter is received, i.e. open air, floor, ceiling, etc., little to no backscatter is detected and the resulting voltage sent through the device by the CPU is near zero. When a large amount of backscatter is received, i.e. when the device is above the skin but not a vein ("no vein scenario"), the resulting backscatter is greatest, and the voltage is greatest. Between those two results is the calibration point where some backscatter is received and a blood vessel is detected. This calibrated range will depend on the power transmitted by the infrared transmitter, the spacing of the transmitters and receivers, and the distance above the skin, among other variables.

Within that calibrated range the LED lights on the upper surface of the device can be calibrated to illuminate to various illumination levels in proportion to the backscatter received, and therefore the size of the blood vessel. It is known that larger blood vessels will absorb more infrared energy than will smaller blood vessels (and skin absorbs very little). Therefore, the more backscatter received within the calibration setpoints the smaller the blood vessel being detected.

Figure 3:
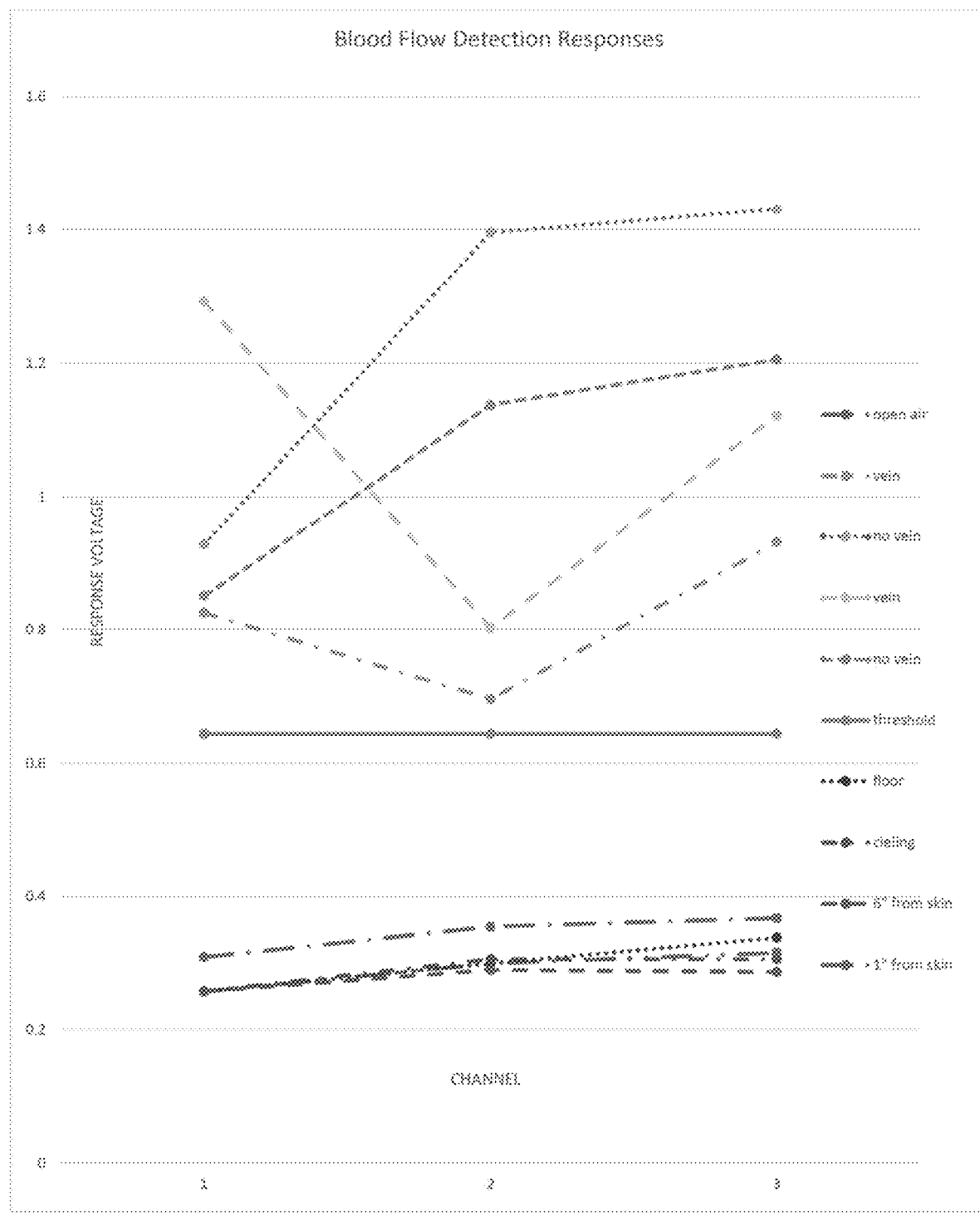
FIG. 3 depicts a chart of the test results from FIG. 2.
Figure 4:
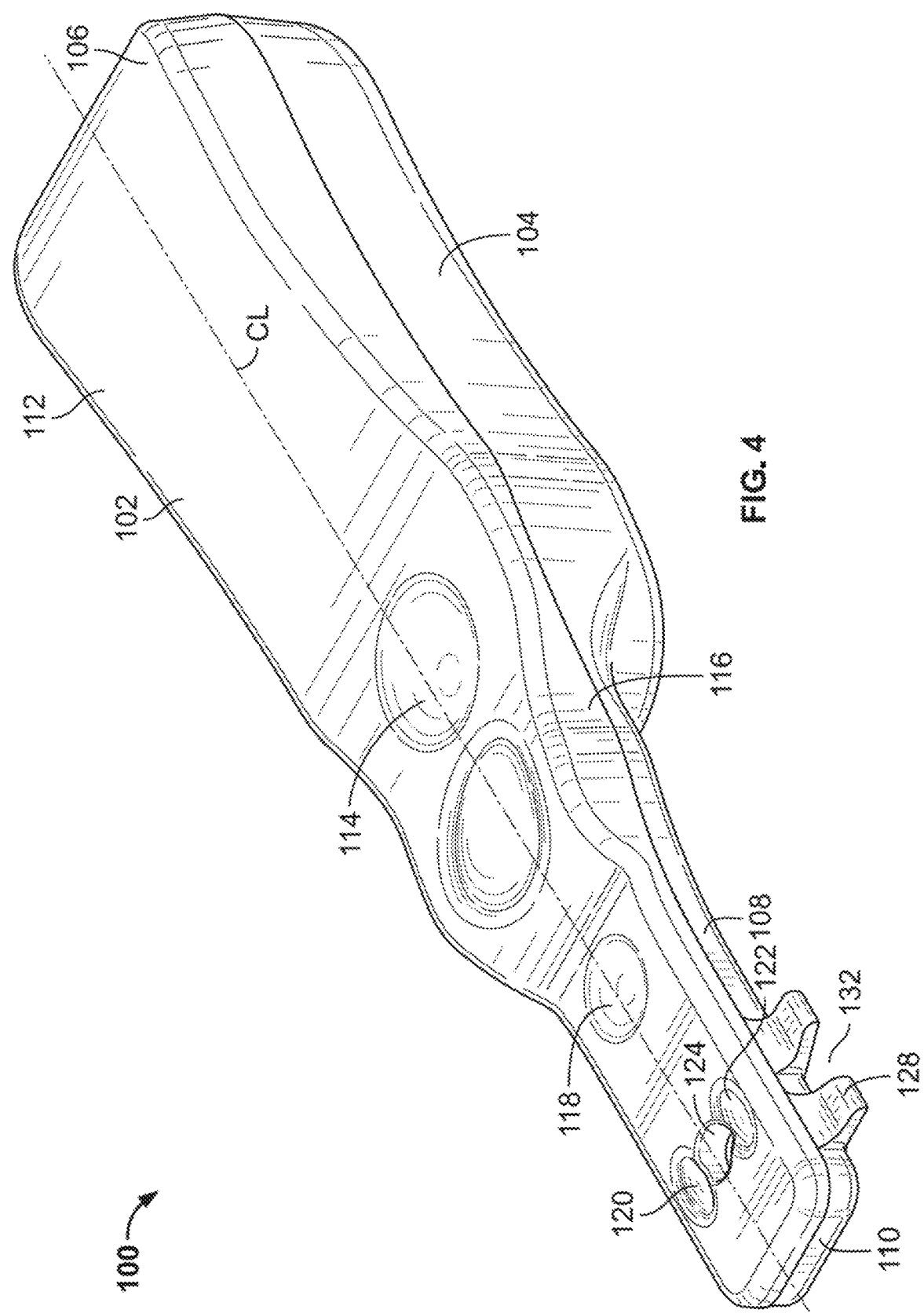
FIG. 4 depicts a perspective view of a medical device in accordance with a first embodiment of the present invention.
Figure 5:
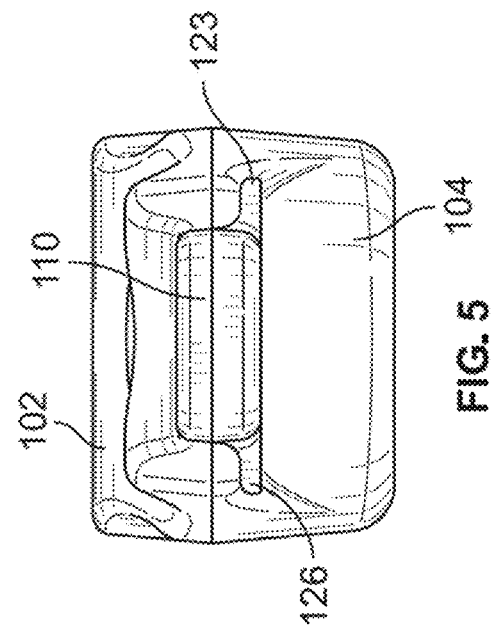
FIG. 5 depicts a frontal view of the device of FIG. 4.
Figure 6:
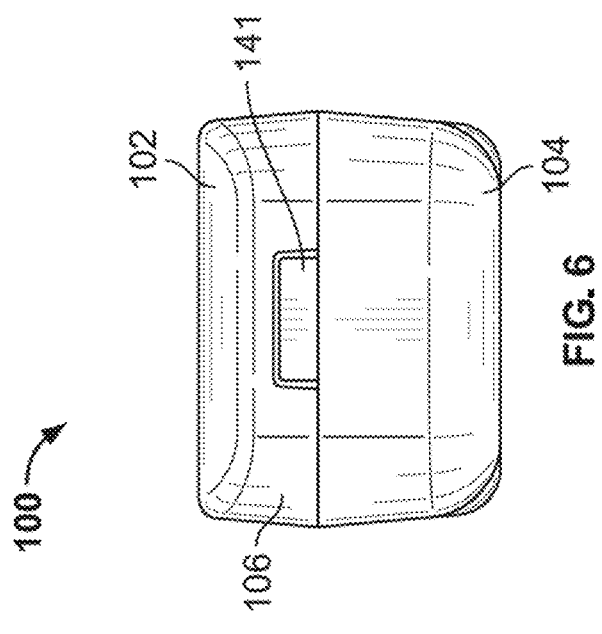
FIG. 6 depicts a rear view of the device of FIG. 4.
Figure 7:
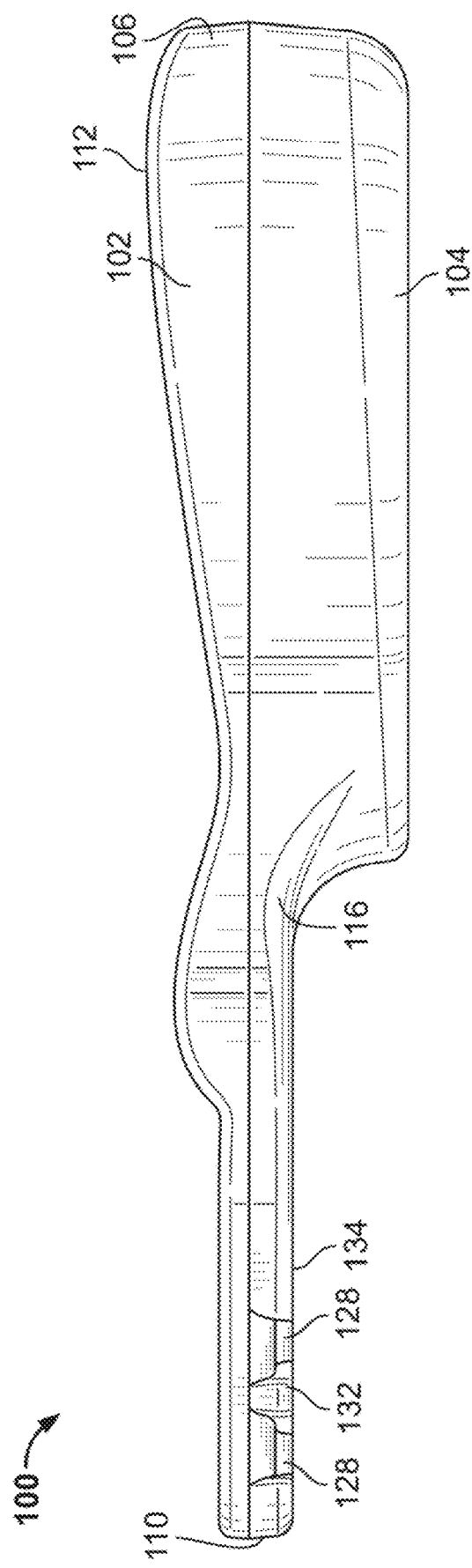
FIG. 7 depicts a left side view of the device of FIG. 4.
Figure 8:
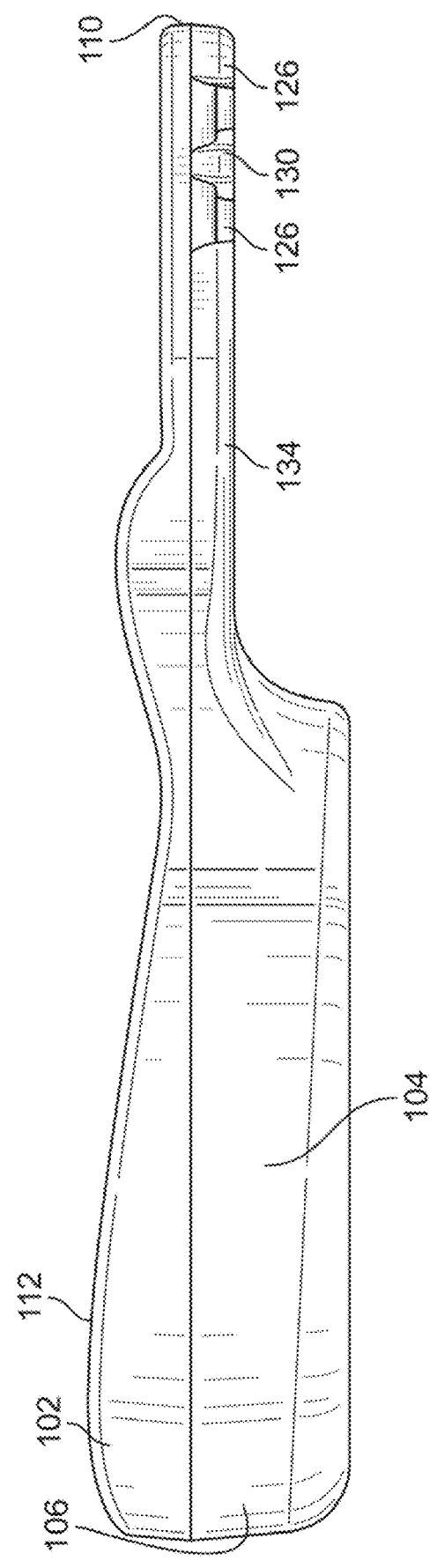
FIG. 8 depicts a right side view of the device of FIG. 4.
Figure 9:
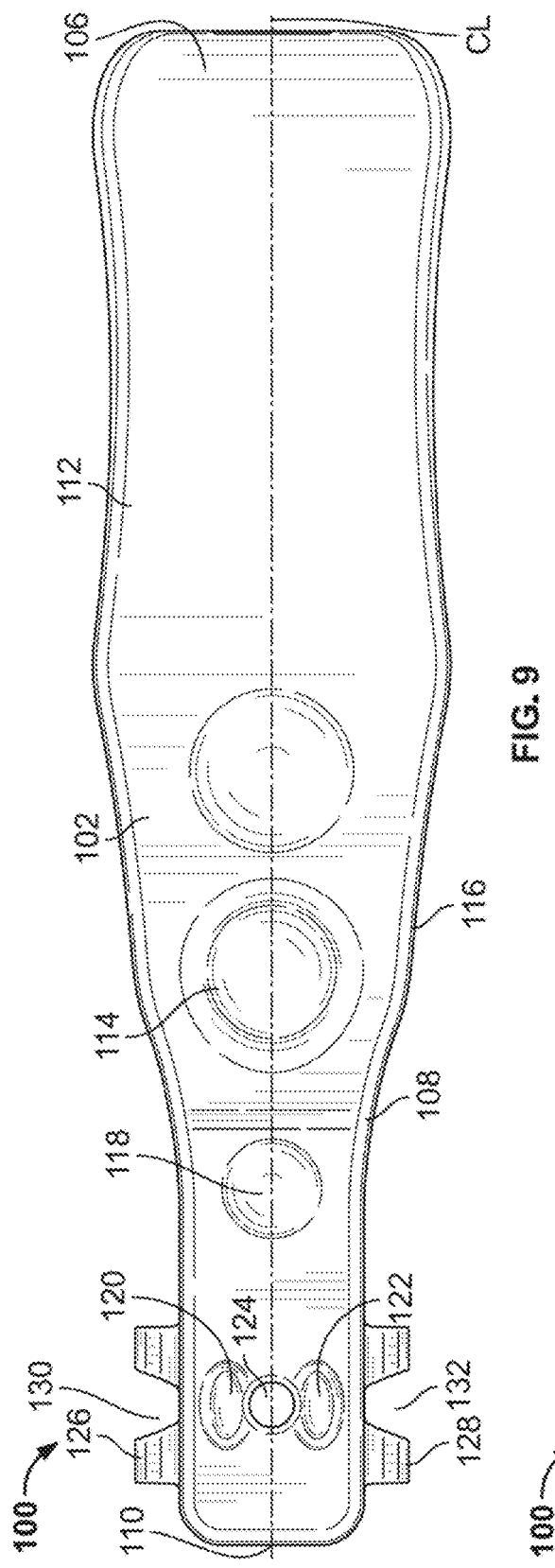
FIG. 9 depicts a top view of the device of FIG. 4.

The table of FIG. 2 is shown graphically in the chart of FIG. 3.

It will be appreciated that channel 2 (or the B channel), receives very little responsive voltage (backscatter) when pointed toward the floor, ceiling, 1" from the skin, 6" from the skin, or open air. This data is represented below the threshold line at 0.644 volts and is a result of very little backscatter being detected by the receiver. In the meantime, when positioned on the skin (or within +/−⅛"), the infrared light is reflected back to the receiver as backscatter and the resulting voltage sent through the device by the CPU is approximately 1.13 and 1.4 in two separate tests. Both results are represented by generally straight lines or inverted "V" shapes.

When the receiver is placed on the skin above a blood vessel, the responsive voltage for Pair B is in the 0.7 to 0.8 range. This is explained in the fact that the blood vessel absorbs some of the infrared signal resulting in reduced backscatter. It is this 0.7 to 0.8 backscatter voltage range, and the presence of a "V" shape as compared to the two outer channels, that indicates the presence of a blood vessel in the device tested, and in particular embodiments, the inferior alveolar nerve (IAN) which runs in a bundle with the inferior alveolar vessels. This bundle is only exposed for a short distance before it disappears into bone (mandible) and is not detectable. Other devices having different transmitter/receiver spacing or different infrared power transmission may be calibrated to different voltage ranges. The divergence between the voltage of the middle pair and the voltage of the two outer pairs may be used to calibrate the device.

Using this and similar testing, the device can be programmed to provide indication for certain size blood vessels, for example focusing on those surrounding the inferior alveolar nerve. In one embodiment of the invention having outputs levels between 0 and 100, the threshold may be set at between 10 and 70 with a preferred threshold established at between 30 and 40. Using 30 as an example, that means when the power differential, or divergence, of Pairs A and C are 30 points above the level indicated by Pair B the device will indicate the presence of a blood vessel. In this regard, the setting of 30 would be considered more sensitive than settings greater than 30 and less sensitive than settings of less than 30.

In some embodiments, the device may be user programmable to change these divergence settings (e.g. between 30 and 40) such that a user can adjust the calibration parameters, and therefore the sensitivity of the device. This is particularly useful in accounting for various skin characteristics of a patient, including level of subcutaneous fat and skin tone. Accordingly, if a patient has fatty tissue or dark skin, the caretaker may enter a calibration that differs from the standard calibration used for lighter skin and non-fatty tissue patients, which generally requires less sensitivity. In most cases, only two preset calibrations need to be incorporated such that a caretaker only needs to switch between the two preset calibration settings. This can be achieved via software with a simple push button or dial. In other embodiments, the device may be configured such that calibration may be more finely tuned by a caretaker. In these embodiments a rheostat may be provided for near infinite adjustment. Alternatively this can also be achieved through software.

Devices may also be configured such that each of the channels must receive a minimum reading for the device to indicate the presence of a blood vessel. In that regard, if one of the outer channels has a higher reading than the middle channel but the other outer channel has a very low or zero reading, the device will recognize that no blood vessel is present (and indeed the device may be misplaced away from the skin of a patient), and will not trigger a positive result.

In further embodiments, there may be a single emitter/receiver pair or more than three emitter/receiver pairs. In the case of the single emitter/receiver pair device, the pair may be calibrated such that the return of voltage within a calibrated range indicates the presence of a blood vessel. In the case of pairs greater than three, the device preferably includes an odd number of pairs so as to maintain a middle pair. Where there are an even number of pairs, the midpoint between the middle two pairs may be used as the central location of a blood vessel. Thus, when the two middle pairs return approximately the same resultant voltage, and the outer pairs are within certain calibrated ranges, the device will indicate the presence of a blood vessel.

In addition to human patients, the devices herein can also be utilized on animals when properly calibrated. That is, the hair (or fur) or relatively thick skin of an animal will not interfere with use of the device so long as the strength of infrared light emission is sufficient.

It goes without saying that the devices are intended to detect blood vessels traveling perpendicular to the long axis of the device (identified hereinafter as the centerline). Thus the device must be used in this manner. Ideally, a caretaker positions the device in an approximate location perpendicular to the expected path of a target blood vessel. The caretaker then slowly moves the device toward the expected location until the indicator lights illuminate properly. It may also be helpful at times to overshoot the blood vessel and then return to truly hone in on its location.

It will also be appreciated that the LED indicator lights may be configured to illuminate with the brightness corresponding to the "closeness" of the received voltage to the threshold. Thus, as an example, vein line shown in dot-dash form (fourth down) will have a central LED (channel 2) which is brighter than channels 1 and 3 when directly over a vein (or artery). Alternatively, the device can be configured to provide the actual voltage readout, or some representation thereof, for example configuring the voltage to display as a strength scale from 1 to 10, with 10 (or alternatively 1) being indicative of either positioning directly over a blood vessel or positioning over a very large blood vessel, per device programming and calibration.

As discussed above, the paired sensors are preferably energized serially to detect backscattered infrared light emitted from only one emitter. The speed of the serially emitted and received infrared signals is preferably calibrated to reduce flickering of the LED lights and to avoid unnecessarily slow lag times. In certain embodiments, this speed can be varied by the caretaker in the field.

The device can be configured with a single housing, particularly in the "medical" version, or the device may be configured in multiple housings, such as in the "dental" version. Generally the dental version will house the first portion of the device, with the infrared emitters and detectors, within a first housing referred to herein as the detector section. The detector section will connect with the second housing of the device, that containing the CPU, rechargeable battery, as well as other electronic components, all in a sealed housing referred to herein as the brain section. Typically the housings will be plastic injection molded but could be manufactured by other means, such as 3D printing or other additive manufacturing technique. The housings may also be made of metal such as medical grade stainless steel or titanium.

The detector section is designed in a fashion which allows the entire section to be pre-sterilized without any damage to its electronic components. This section may be used only as a single disposable item, or can be sterilized after use and reused. Alternatively, the detector section may be protected from bodily fluids such as with a plastic covering. In this manner the covering may be discarded after use (or itself potentially sterilized and reused). In the meantime, the brain section is intended to remain outside the body and reused with multiple patients.

For the medical use device, both the detector section and brain section are located in a single housing which is designed for reuse. Typically this housing need not be sterilized after each use, but may be. It may also be covered with a covering such as mylar film as will be discussed.

In one example of a suitable device, the IR output may be 16 mW/sr at 940 nm with an IR sensor of 0-2 mW/cm2->0-3.2 uA at 940 nm. The IR sensor is converted to voltage via a 100 k resistor where the voltage is between 0 v and 0.32 v. An analog to digital converter is provided at 10 bit 3.23 mV/bit (100 counts 2 mW/cm^2).

In the example device, a skip detection threshold is set at greater than 200 counts to enable vein detection (≈4 wM/cm^2) and a vein detection threshold is set at 20-100 (0.4-2 mW/cm^2), i.e. left-center>threshold and right-center>threshold. Sensor pairing (channel to channel) is set at 5.5 mm.

Power levels of the devices are preferably set as low as practical to avoid unnecessary battery draw while still providing adequate power. Additionally, it should be noted that the devices provide zero harmful radiation to animal or human skin in operation.

No size of devices is mandated other than to fit within the parameters of this specification. In general, however, the devices are designed to be small and portable such that they can fit easily in a caretaker's shirt pocket.

Medical Use Device

Figure 10:
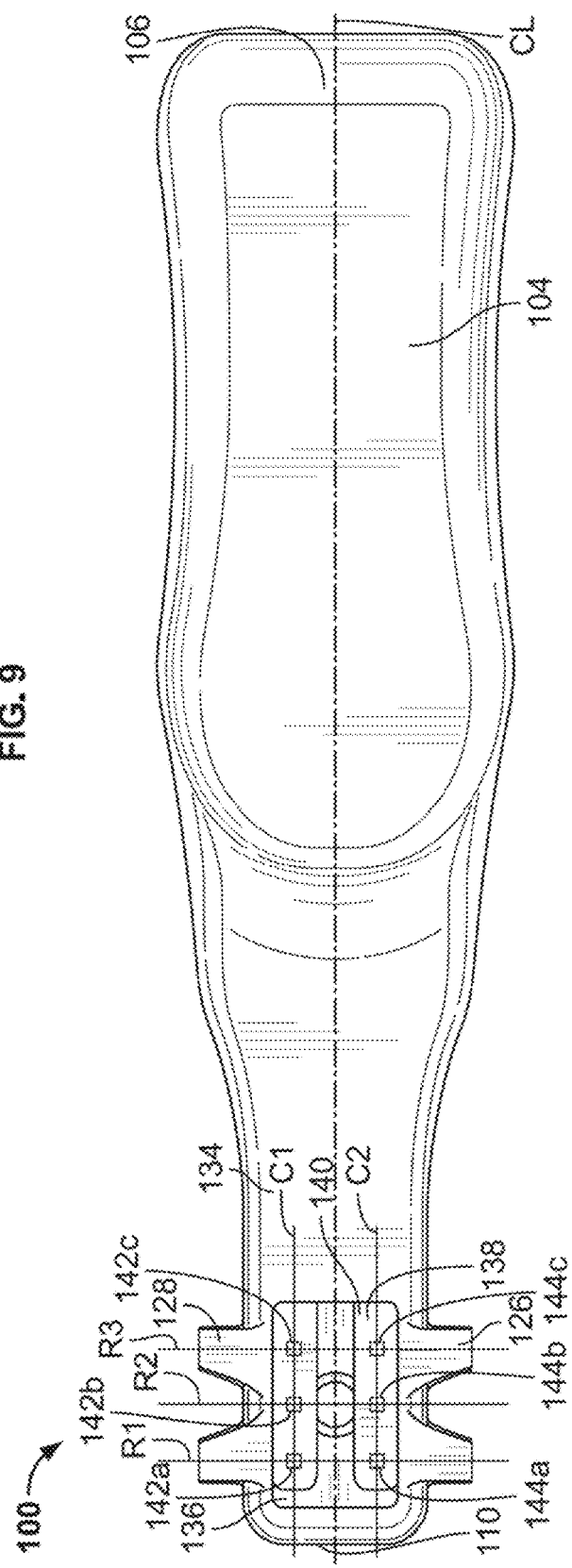
FIG. 10 depicts a bottom view of the device of FIG. 4.
Figure 11:
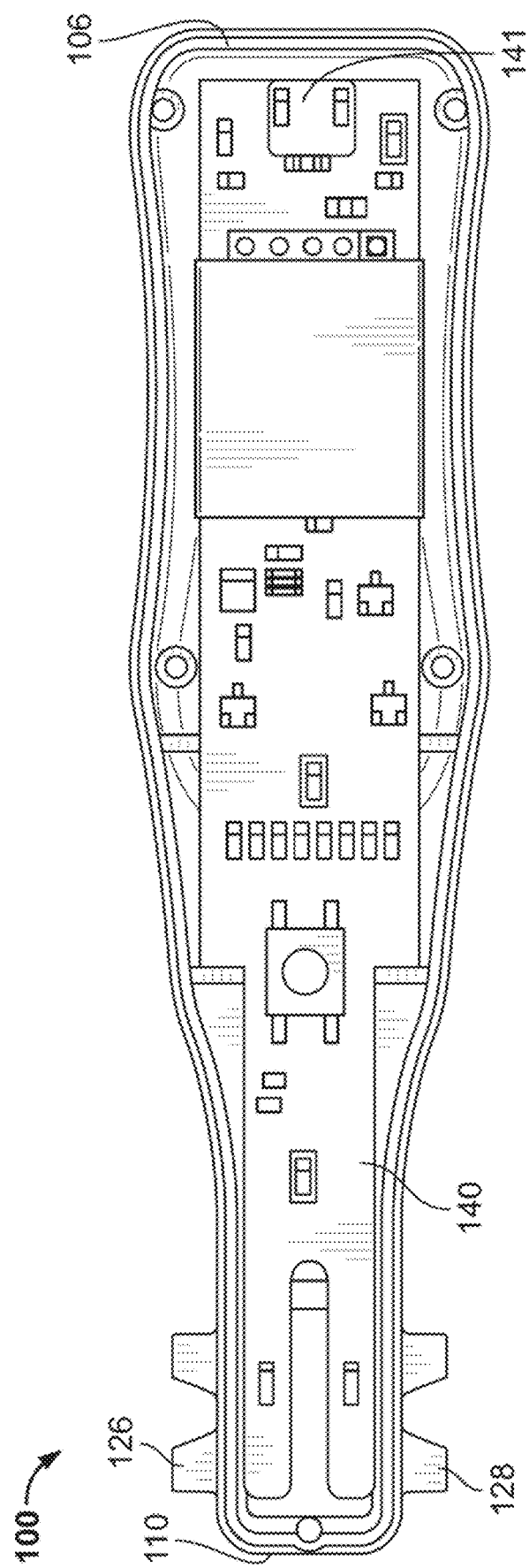
FIG. 11 depicts a cut-away top view of the device of FIG. 4.

FIGS. 4-11 depict various views of an exemplary medical use device 100 in accordance with one embodiment of the present invention. As shown most clearly in FIG. 1, the medical use device 100 is configured from two pieces, an upper piece 102 and a lower piece 104. The two together are designed such that the proximal portion 106 is generally bulbous, fitting ergonomically and comfortably within the hand of a caretaker while the distal portion 108 tapers more narrowly and extends to a distal end 110. In addition to providing comfortable use, it will be appreciated that the bulbous nature and ergonomic design of the proximal portion 106 also leaves interior space for various electronics needed for the medical use device 100 to operate as shown in FIG. 11.

Located on the top surface 112 of the upper piece 102 are various controls and readouts. Specifically, an on/off button 114 is located at the transition 116 between the proximal portion 106 and distal portion 108 of the medical use medical use device 100. A single LED 118 is located on the top surface 112 of the upper piece 102. This single LED 118 is illuminated when the medical use device 100 is powered on and is extinguished when the device is powered off. Closer to the distal end 110 of the medical use device 100 are a pair of LEDs 120, 122. Each of LEDs 120, 122 are on opposite sides of an aperture 124 positioned along a centerline CL of the medical use device 100 and sized larger than, preferably by approximately 2-3 times, the diameter of a hypodermic needle. As will be discussed more fully below, one primary purpose of aperture 124 is to permit a caretaker to visually observe and have physical access to a blood vessel traversing the aperture 124.

The distal portion 108 of the medical use device 100 also includes a pair of wings 126, 128. Each of the wings 126, 128 include its own slot or recess, 130, 132, extending along an axis normal to the centerline CL. The primary purpose of wings 126, 128 and slots 130, 132 is physical manipulation of a blood vessel, as will be discussed hereinbelow.

Additionally, it is preferred that the slot be V-shaped. The V-shape design allows the caretaker to visually align the device adjacent and perpendicular to the vein in patients where veins are visible. This identifies the alignment of the detectors automatically perpendicular to the vein for proper detection. This aspect is helpful in that the device must be perpendicular to a blood vessel for proper reading.

Referring back to LEDs 120, 122, it will be appreciated that the medical use device 100 is configured such that both illuminate when a caretaker places the medical use device 100 in a position such that the patient's blood vessel being sought, detectable given the calibration parameters of the medical use device 100, is directly located in Position B as discussed previously with respect to FIG. 1, Position B being when the blood vessel is within both slots 130 and 132. While various brightness and colors may be used for LEDs 120, 122, in the medical use devices it has been found that a relatively dim red LED is most efficient. The brightness may also be caretaker adjustable. In some embodiments, the brightness might represent the relative proximity and relative size of the blood vessel. That is, the larger the blood vessel and the closer same is to Position B of FIG. 1, the brighter the LED will illuminate.

Referring to FIG. 10, the medical use device 100 also includes a bottom surface 134. At the distal portion 108, there is provided a cutout 136 exposing an underside 138 of a circuit board 140 disposed within the medical use device 100. Mounted on the circuit board 140 and facing toward the cutout 136 are three infrared light emitters 142a, 142b, 142c and three infrared light receivers 144a, 144b, 144c arranged in pairs. In other embodiments there may be more or less pairs, but preferably there is always an odd number such that at least one of the pairs, and preferably a middle one of the pairs, is aligned with the slots 130, 132 of wings 126, 128.

The three infrared light emitters 142a, 142b, 142c are adapted to emit infrared light from the cutout 136 and expose said light on a patient's skin. The three infrared light receivers 144a, 144b, 144c are adapted to receive backscattered infrared light reflected from the patient's skin. As discussed previously, the backscattered signal is converted to a voltage and a properly calibrated CPU can identify when the medical use device 100 is positioned directly above a blood vessel, represented by Position B of FIG. 1.

Preferably, and as shown, the three emitters 142a, 142b, 142c and the three receivers 144a, 144b, 144c are arranged in pairs along equally spaced rows, R1, R2, R3, including a middle row, R2, each equally spaced row extending perpendicular to the centerline CL of device 100. The middle row R2 is aligned with said aperture 124.

The three infrared light emitters 142a, 142b, 142c and three infrared light receivers 144a, 144b, 144c are also arranged in two columns, C1, C2 where the columns extend along axes equally spaced and parallel to the centerline CL.

Equal spacing of the rows and columns is highly preferred as such geometry aids tremendously in calibration of the medical use device 100. It has also been found that spacing must be such that it is not so wide as to straddle two blood vessels and not so narrow as to have the outside pairs too close to a blood vessel when the inside pair is overtop. Also, crosstalk will interfere with readings if diodes are too close and not sequentially energized.

Referring back to FIG. 11, it will be appreciated that the circuit board 140 is preferably configured as a single unit. Among other components the circuit board 140 includes a central processing unit and a battery.

One of the salient features of the circuit board is the inclusion of a charge port 141 at the proximal portion 106, the charge port adapted to charge a battery (not shown) included within the medical and dental use device 100. The charge port is preferably configured as a micro USB port or similar.

Figure 12:
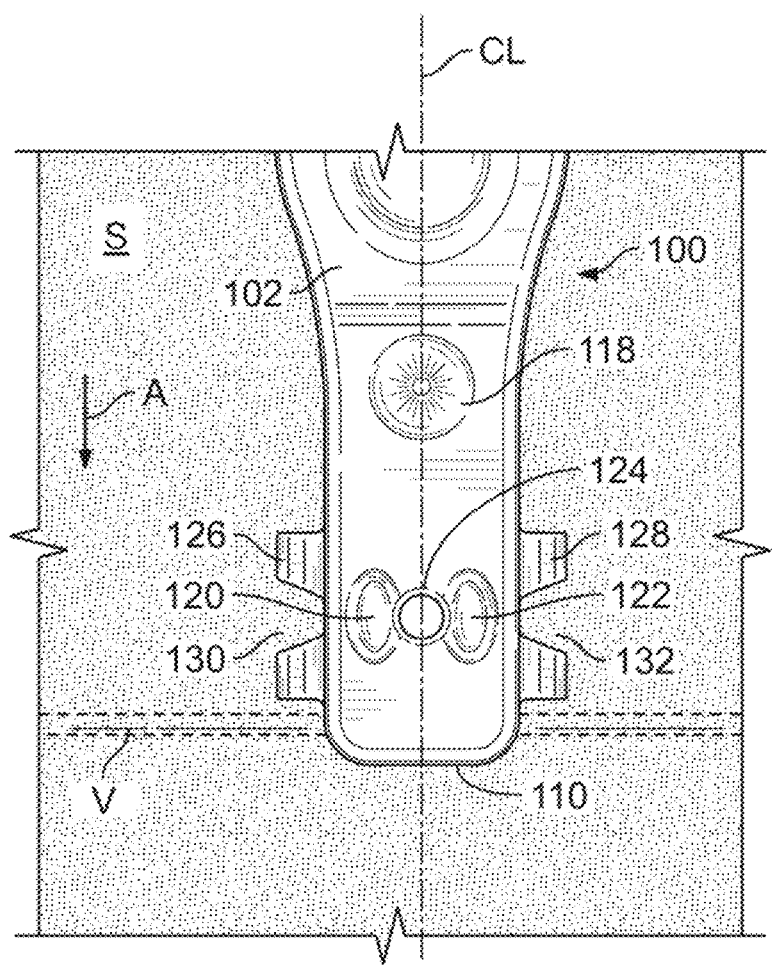
FIGS. 12-17 depict top views of the device of FIG. 4 in various states of use.

The distal portion 108 of device 100 is shown in an initial stage of typical use in FIG. 12. As shown, the medical use device 100 is positioned upon the patient's skin S such that the bottom surface 134 gently contacts the skin or hovers just slightly above it. The positioning is such that the target blood vessel V is generally perpendicular to the centerline CL of the medical use device 100. The medical use device 100 is then moved toward the general area of the target blood vessel V as indicated by arrow A.

Figure 13:
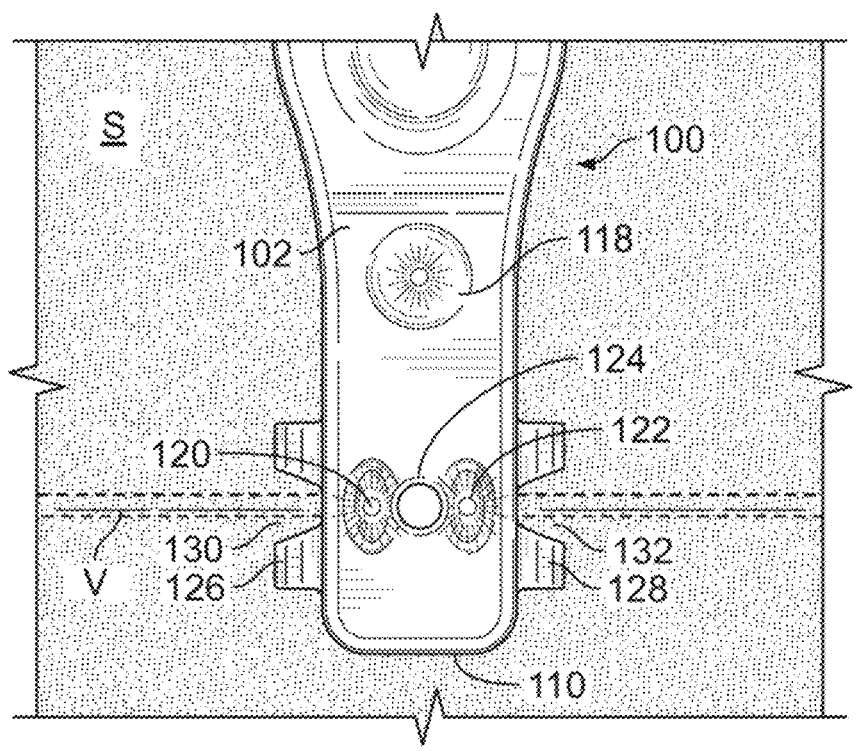

With the medical use device 100 energized, the emitters will emit infrared light and the sensors will begin to serially sense backscattered infrared light bouncing off the skin. As the medical use device 100 is moved toward the position shown in FIG. 13, particularly with the vessel V positioned within slots 130, 132, LEDs 120, 122 will begin to illuminate. In certain embodiments of the invention, the CPU can be calibrated such that the LEDs illuminate with greater intensity the closer the vessel V is to being within slots 130, 132. In other embodiments, and in the preferred embodiment, the LEDs are simply on/off as it can be difficult in certain lighting to ascertain variable LED intensities. Either way, the LED indicators may also be supplemented with audible notes, if desired. In still further embodiments, the LED indicators may be completely replaced with an audible tone to indicate the presence of a blood vessel. Thus, the device may indicate presence of a blood vessel via visual or aural means.

If a caretaker overshoots the vessel V, (s)he can also move the medical use device 100 opposite to the direction of arrow A. Once the target blood vessel V is confidently positioned directly within the slots 130, 132, the caretaker has various options for either marking the blood vessel for later penetration or for directly penetrating it.

Figure 14:
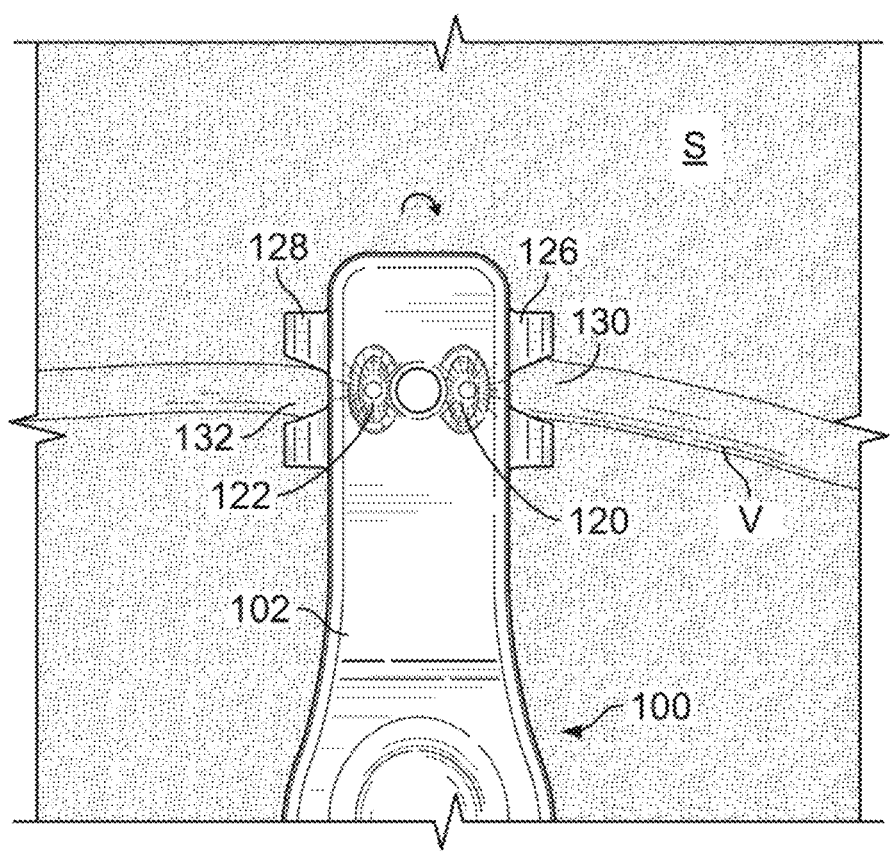

For example, as shown in FIG. 14, the caretaker may rotate the medical use device 100 about the centerline CL approximately 15-60 degrees such that a wing, in this case wing 126, captures the blood vessel V within its slot 130. This will prevent the blood vessel V from shifting or moving during penetration. This technique is particularly useful for penetration of a blood vessel within a patient's dorsal venous network of the hand, which are known to move readily.

Figure 15:
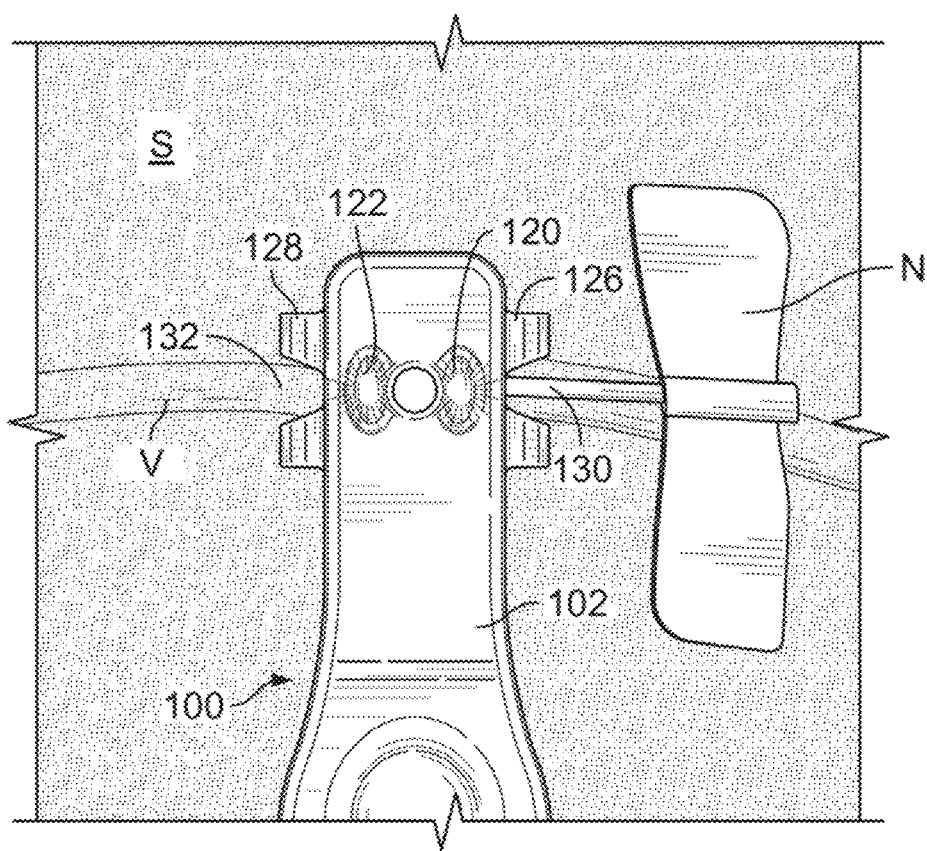

In a second option shown in FIG. 15, the caretaker may simply hold the medical use device 100 in place and penetrate the vessel with a winged infusion set, or butterfly needle N at one of the slots 130, 132, in this case 130.

Figure 16:
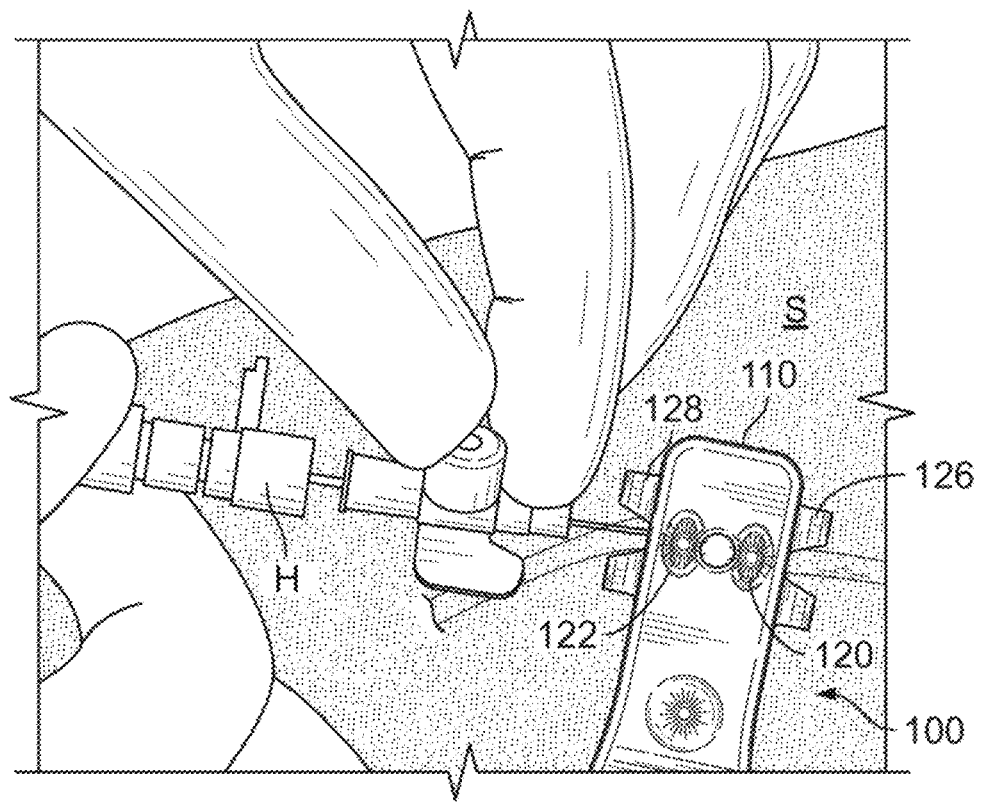

Similarly, and as shown in FIG. 16, the caretaker may insert a standard hypodermic needle H (or IV cannula) into a vessel V with the medical use device 100 hovering over the vessel.

Figure 17:
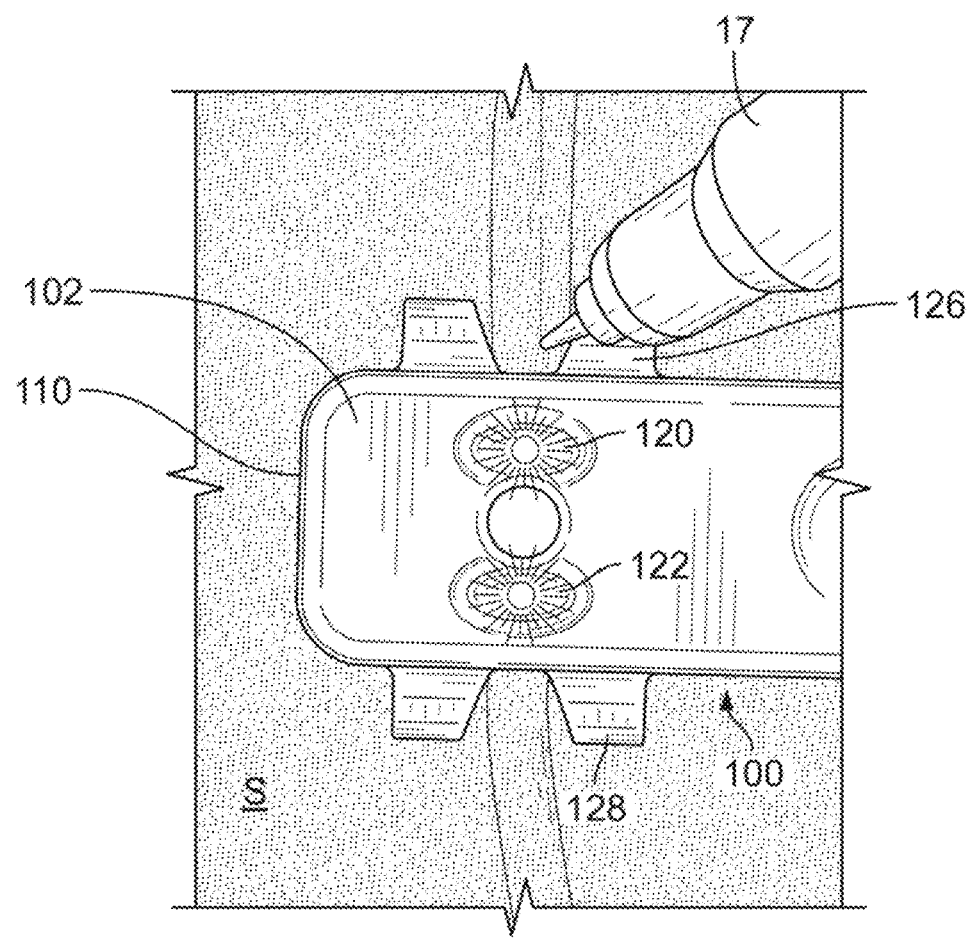

In a still further option shown in FIG. 17, the caretaker may mark the blood vessel V with a marking device, such as a standard pen or marker M, for later reference. Typically, the marking may be achieved at both slots 130, 132, and/or aperture 124. With at least two of those positions marked, the axis of the blood vessel is revealed.

Although not shown, there remains the final option of direct vessel penetration through aperture 124.

Dental Use Device

FIGS. 18-26 depict various views of an exemplary dental use device 200 in accordance with a second embodiment of the present invention. In many ways the configuration of the dental use device 200 is similar to that of the medical use device 100 discussed previously. However, a main difference is that the dental use device is designed such that its distal and proximal portions can be separable (it is noted that in some embodiments they may not be separable). In this regard the distal end, that end which enters a patient's mouth, can be discarded or sterilized while the proximal portion, which remains outside the patient's mouth, can be reused after general cleaning.

Figure 18:
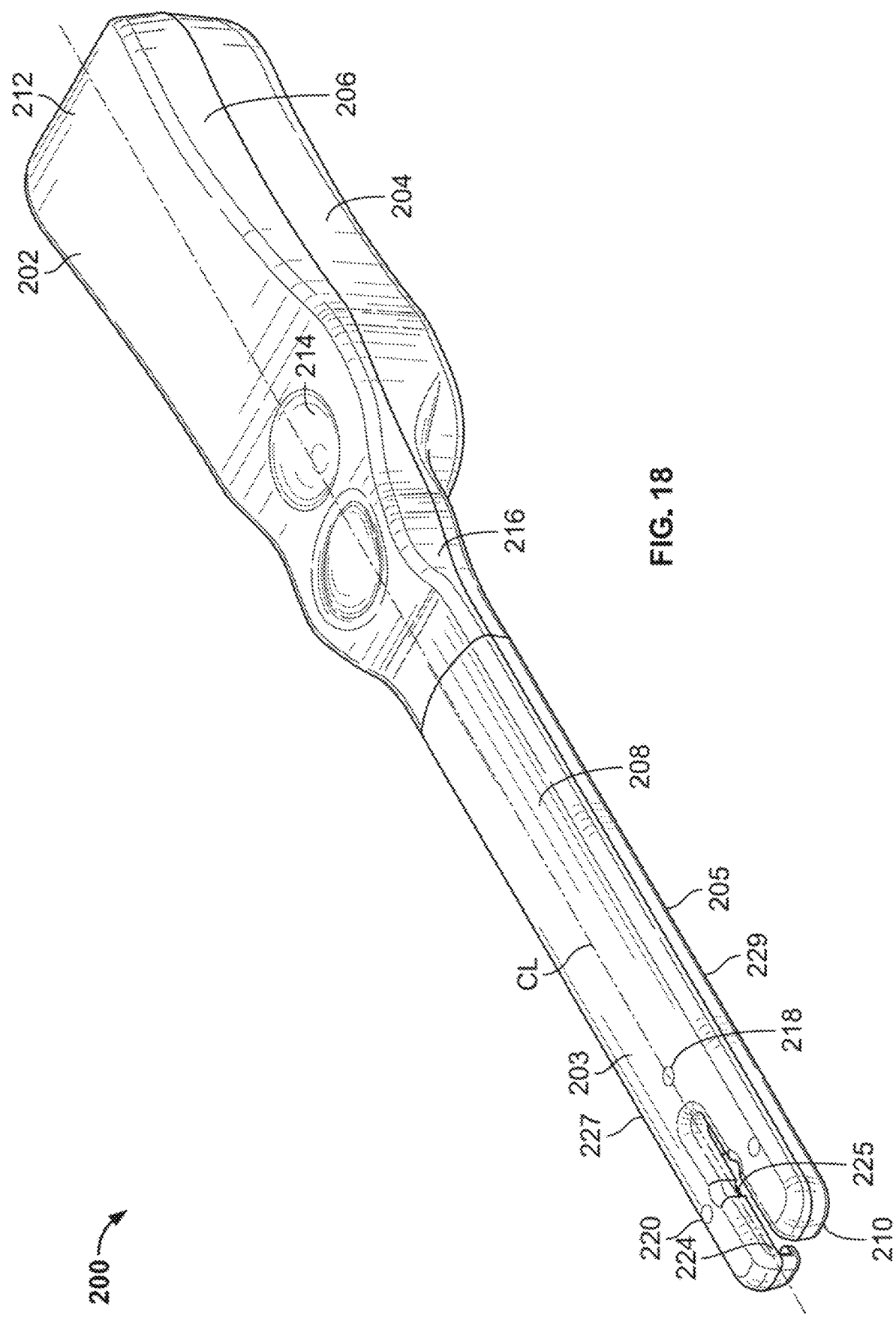
FIG. 18 depicts a perspective view of a dental device in accordance with a second embodiment of the present invention.
Figure 20:
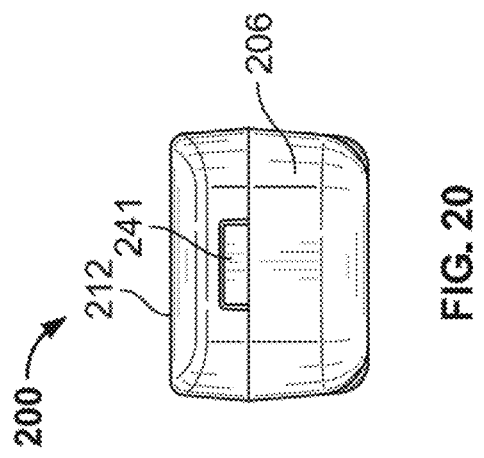
FIG. 20 depicts a rear view of the device of FIG. 18.
Figure 19:
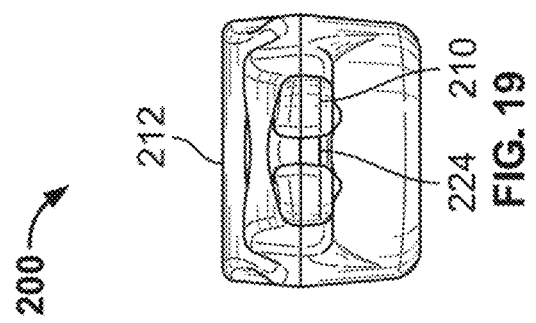
FIG. 19 depicts a frontal view of the device of FIG. 18.

As shown in FIG. 18, the dental use device 200 is configured from four pieces, an upper proximal piece 202, an upper distal piece 203, a lower proximal piece 204, and a lower distal piece 205. It will be appreciated that the upper proximal piece 202 and the lower proximal piece 204 combine to form a generally bulbous proximal portion 206 such that it fits comfortably within the hand of a caretaker. Upper distal piece 203 and lower distal piece 205 combine to form the distal portion 208 which is much narrower and longer than the proximal portion 206. It will be appreciated that the distal portion 208 is shaped in this manner so that it fits comfortably deep within a patient's mouth, with the distal end 210 adapted to reach all the way to and slightly beyond the inferior alveolar neurovascular bundle in its exposed section medial to the ramus of the mandible before entering the mandible.

Figure 26:
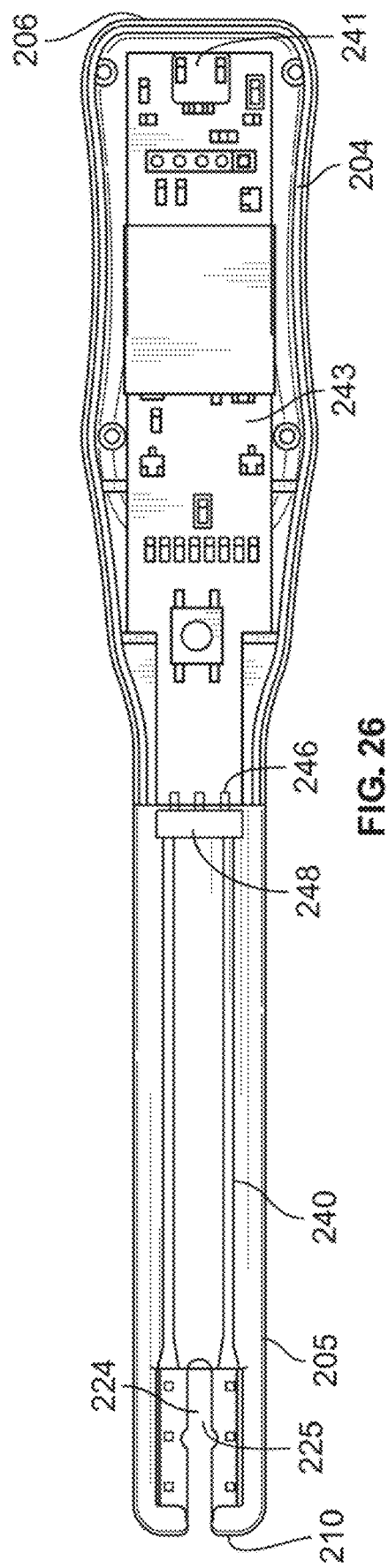
FIG. 26 depicts a cut-away top view of the device of FIG. 18.

In addition to providing comfortable use, it will be appreciated that the bulbous nature of the proximal portion 206 also leaves interior space for various electronics needed for the dental use device 200 to operate. An exemplary circuit board 240 is shown in FIG. 26, within the dental use device 200.

Located on the top surface 212 of the upper piece 202 are various controls and readouts. Specifically, an on/off button 214 is located at the transition 216 of the proximal portion 206 and distal portion 208. A single LED 218 is located on the top surface 212 of the upper distal piece 203. This single LED 218 is illuminated when the dental use device 200 is powered on and is extinguished when the device is powered off. Closer to the distal end 210 of the dental use device 200 are a pair of LEDS 220, 222. Each of LEDs 220, 222 are on opposite sides of a slotted aperture 224 positioned along a centerline CL of the dental use device 200. The slotted aperture is a slot starting at the distal end 210 of the dental use device 200 and extending toward the proximal portion 206 thereof. Within the slotted aperture 224 is a circular portion 225 sized larger than, preferably by approximately 2-3 times, the diameter of a hypodermic needle. As will be discussed more fully below, one primary purpose of circular portion 225 is to permit a caretaker to have physical access to blood vessels traversing perpendicular to the slotted aperture 224 (in line with the LED lights).

Unlike the medical use device 100, the dental use device 200 does not include wings. Rather, the sides 227, 229 of the distal portion 208 of the dental use device 200 are smooth and flat so as to not cause patient discomfort.

Referring back to LEDs 220, 222, it will be appreciated that the device is configured such that both illuminate when a caretaker places the dental use device 200 in a position such that the patient's blood vessels being sought, detectable given the calibration parameters of the dental use device 200, is directly located in Position B as discussed previously with respect to FIG. 1, Position B being when the blood vessel is below a middle pair of infrared detectors as will be discussed. While various brightness and colors may be used for LEDs 220, 222, in the dental use devices it has been found that a relatively bright blue LED is most efficient due to the darkness intraorally. This differs from the medical use device which benefits from relatively dim red LEDs lights. The brightness may also be caretaker adjustable.

Referring to FIG. 24, the dental use device 200 also includes a bottom surface 234. At the distal portion 208, there is provided a cutout 236 exposing an underside 238 of a circuit board 240 disposed within the dental use device 200. Mounted on the underside 238 of circuit board 240 and facing toward the cutout 236 are three infrared light emitters 242*a*, 242*b*, 242*c* and three infrared light receivers 244*a*, 244*b*, 244*c* arranged in pairs at appropriate distance apart to eliminate cross talk. In other embodiments there may be more or less pairs, but preferably there is always an odd number such that at least one of the pairs is aligned with the circular portion 225 of slotted aperture 224.

The three infrared light emitters 242*a*, 242*b*, 242*c* are adapted to emit infrared light from the cutout 236 to a patient's skin and the three infrared light receivers 244*a*, 244*b*, 244*c* are adapted to receive backscattered infrared light reflected from the patient's skin, in both cases the skin being inside a patient's mouth. As discussed previously, the backscattered signal is converted to a voltage and a properly calibrated CPU can identify when the dental use device 200 is positioned above a blood vessel. In the case of the dental device, and as will be discussed, the presence of a blood vessel is noteworthy not for identifying the location of the blood vessel itself, but because the inferior alveolar nerve is bundled with a large blood vessel and its location can be better determined by finding that blood vessel group.

Preferably, and as shown, the three emitters 242*a*, 242*b*, 242*c* and the three receivers 244*a*, 244*b*, 244*c* are arranged in pairs along equally spaced rows, R1, R2, R3, including a middle row, R2, each equally spaced row extending perpendicular to the centerline CL. The middle row R2 aligned with said slotted aperture 224.

The three infrared light emitters 242*a*, 242*b*, 242*c* and three infrared light receivers 244*a*, 244*b*, 244*c* are also arranged in two columns, C1, C2 where the columns extend along axes equally spaced and parallel to the centerline CL.

Equal spacing of the rows and columns is highly preferred as such geometry aids tremendously in calibration of the dental use device 200. It has also been found that spacing must be such that it is not so wide as to straddle two blood vessels and not so narrow as to have the outside pairs too close to a blood vessel when the inside pair is over top.

Figure 25:
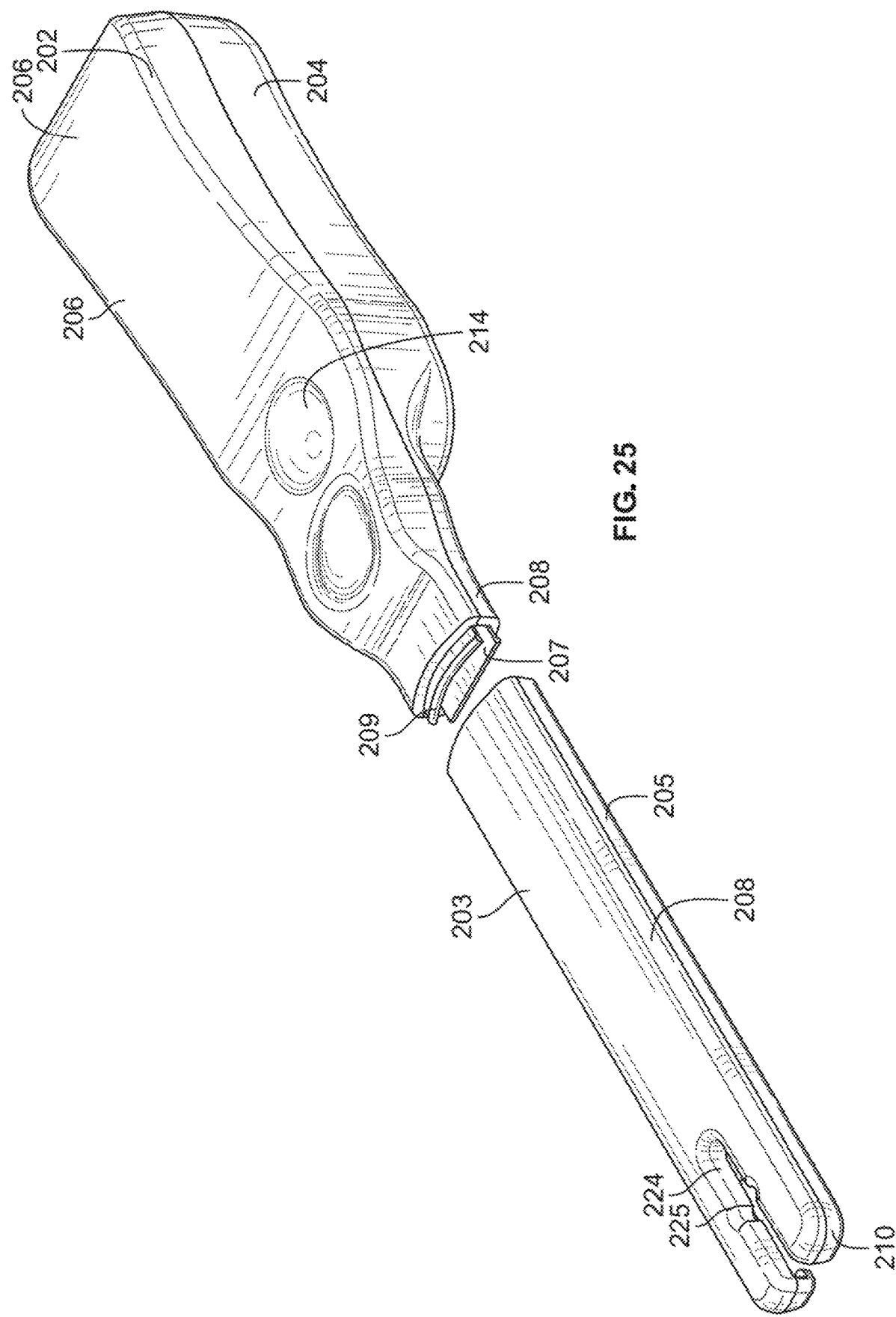
FIG. 25 depicts a partially exploded perspective view of the device of FIG. 18.

The dental use device 200 is designed to be separable. That is, the distal portion 208 is designed to separate from the proximal portion 206. The housing, which as discussed above is typically plastic, may be separable by using simple friction fit connections or various types of interlocking/interference connections. One example is shown in FIG. 25 where two friction fit fingers 207, 209 are adapted to mate with corresponding internal portions (not shown) of the distal portion 208 of the dental use device 200.

Within the housing there are disposed two circuit boards, 240, 243, as shown in FIG. 26. Circuit board 243 has been discussed above, and is disposed within the distal portion 208 of the dental use device 200 and generally has mounted on it the three infrared light emitters 242*a*, 242*b*, 242*c* and three infrared light receivers 244*a*, 244*b*, 244*c*. Circuit board 243 is disposed within the proximal portion 206 of the dental use device 200 and has the remaining electronics mounted in it. As will be discussed, these electronics include at least a battery and central processing unit. The two circuit boards 240, 243 are connectable via a female electronic connection 246 and a male electronic connection 248 (essentially a plug) when the distal portion 208 of the dental use device 200 is connected to the proximal portion 206. In other embodiments, the circuit boards 240, 243 may be configured as a single circuit board with no ability to separate. In this regard, only the housing portions of distal portion 208 and proximal portion 206 are separable. Once separated, the singular circuit board stays with the proximal portion 206 and the distal portion 208 may be discarded and replaced or sterilized for further use.

One of the salient features of the circuit board 240 is the inclusion of a charge port 241 at the distal end 206, the charge port adapted to charge a battery (not shown) included within the dental use device 200. The charge port is preferably configured as a micro USB port or similar.

The mandibular block (inferior alveolar nerve) injection is a routine procedure in a dental office done to anesthetize the entire lower jaw on one side with one injection. Thousands of these injections per day take place just in United States.

The experience of a needle injection is traumatic to most people, especially children. Once anaesthetized the patient and operator are much more comfortable and proper care can be administered.

For most dentists, this injection is challenging. The most common technique for locating the nerve is physical touching. Indeed, misses occur often. Statistically there in only a 40-50% success rate on the first attempt as the neurovascular bundle is not visible and disappears quickly into the bone where conventional anesthetic solution is ineffective.

The present dental device 200 enables a dentist to quickly and easily identify the deep inferior alveolar vessels—part of the mandibular branch of the submandibular neurovascular bundle—before it disappears into the mandible. The dentist detects the location of the inferior alveolar vein by sensing its blood flow, deep in the tissue, before it enters the mesial side of the ramus of a patient's mandible. The identification of the inferior alveolar vein and thus the location of the neurovascular bundle in which it travels, will allow a dentist to know precisely where to inject a local anesthetic solution to gain profound anesthesia in the entire lower quadrant (inferior alveolar nerve block IANB).

The distal portion 208 of device 200 is shown in use in FIGS. 27 to 30. Before addressing those figures, attention is brought to FIG. 31, depicting the mental nerve MN and Inferior Alveolar nerve of a patient. Each of the two procedures of FIGS. 27 to 30 seeks one of these nerves.

Figure 27:
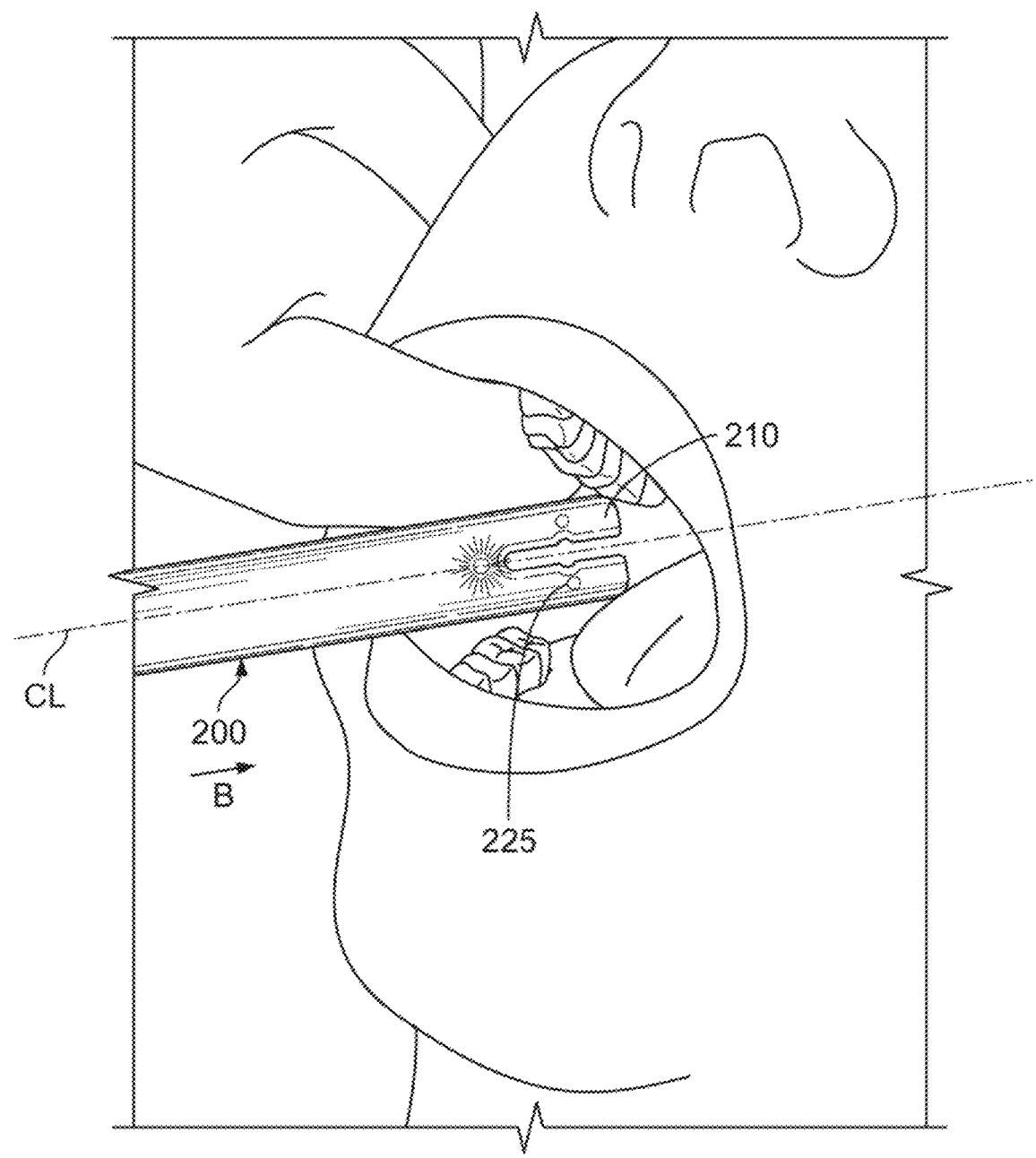
FIGS. 27-30 depict views of the device of FIG. 18 in various states of use; and, FIG. 31 depicts typical anatomy of a human mouth.

As shown in FIG. 27, to seek the IAN, the dental use device 200 is positioned within a patient's open mouth such that the bottom surface (not shown in FIG. 27) gently contacts the skin or hovers just slightly above it in the area of the molars as near to the IAN as possible. In this way the target blood vessel at the IAN will generally be perpendicular to the centerline CL of the dental use device 200. The dental use device 200 is then moved toward the general area of the target blood vessel, in the direction of Arrow B. With the dental use device 200 turned on, the sensors will begin to serially sense backscattered infrared light bouncing off the skin.

Figure 28:
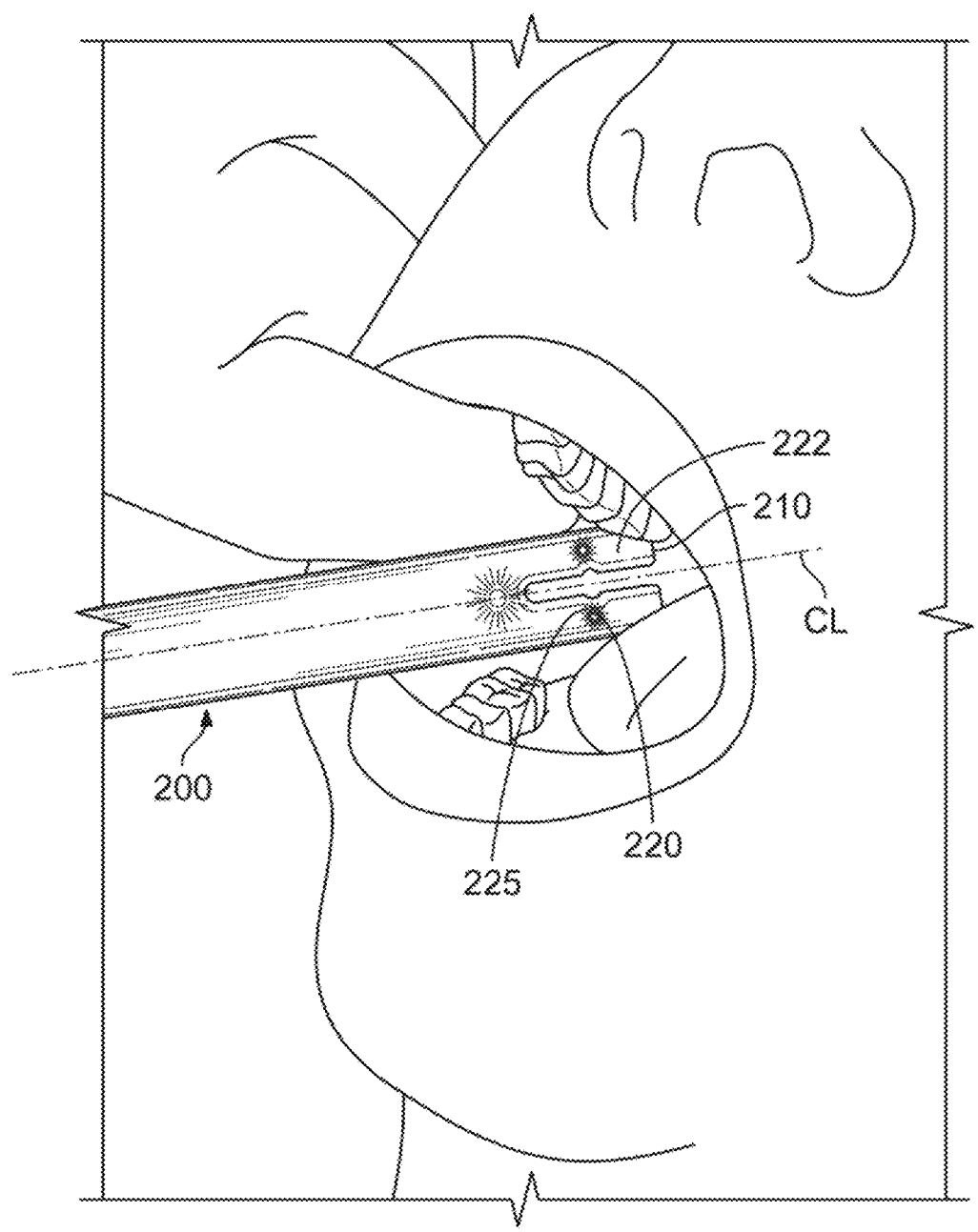

As the dental use device 200 is moved toward the position shown in FIG. 28, and now with the vessel associated with the IAN positioned within the circular portion 225 of slotted aperture 224, LEDs 220, 222 will illuminate. In certain embodiments of the invention, the CPU can be calibrated such that the LEDs 220, 222 illuminate with greater intensity the closer the vessel is to being within the circular portion 225 of slotted aperture 224. In other embodiments, and in the preferred embodiment, the LEDs are simply on/off as it can be difficult in certain lighting to ascertain variable LED intensities. Either way, the LED indicators may also be supplemented with audible notes, if desired. In still further embodiments, the LED indicators may be completely replaced with an audible tone to indicate the presence of a blood vessel. Thus, the device may indicate presence of a blood vessel via visual or aural means.

Once the target blood vessel is positioned within the circular portion 225 of slotted aperture 224, the caretaker will keep the device still and insert a hypodermic needle through the circular portion 225 of slotted aperture 224 and close to the IAN as close proximal infiltration is sufficient to acquire anesthesia. The caretaker may also place the hypodermic needle through the circular portion 225 of the slotted aperture 224 and hold it in place against the skin inside the patient's mouth while simultaneously removing the device 200 by sliding the device out of the mouth such that the hypodermic needle passes entirely through the slot 224. The caretaker may then discard the device 200 and continue with both hands free.

The mandibular nerve exits the mandible at the mental foramen. That can be located in a similar manner as above by detecting the NV bundle, and thus a mental nerve block can be easily achieved by injecting at the exit of the mental nerve in the mandible below the bicuspids. This anesthetizes the anterior segment of the lower arch, eliminating the need to infiltrate (inject) adjacent to each tooth from the bicuspids to the midline.

Figure 29:
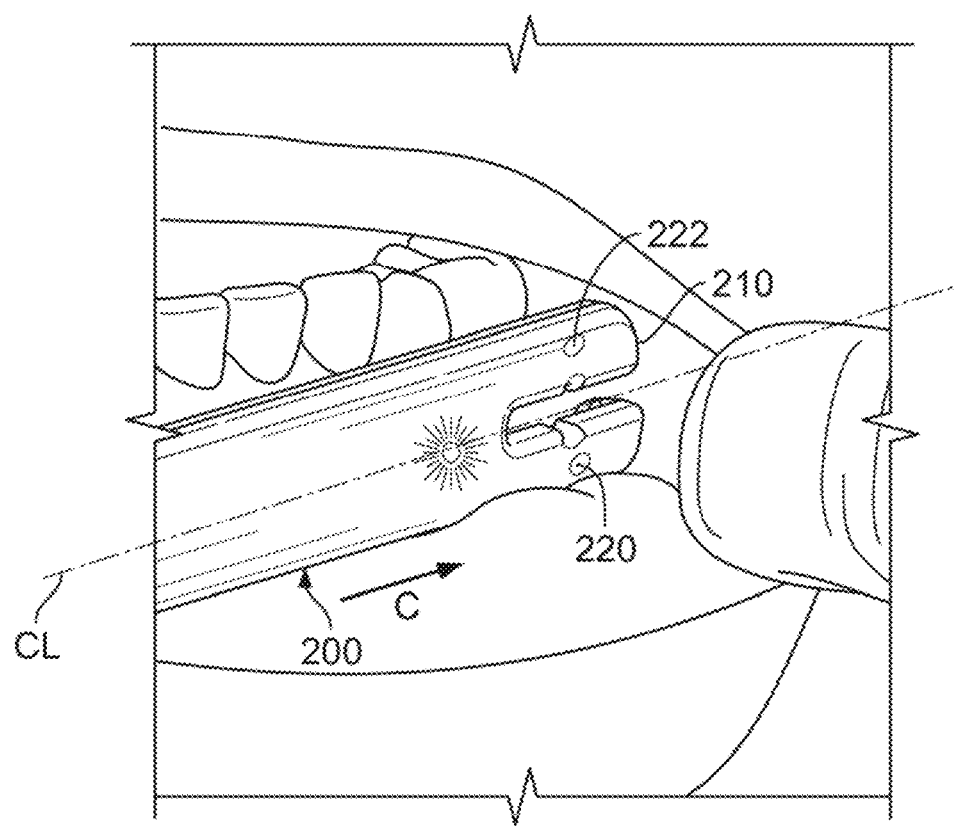
Figure 30:
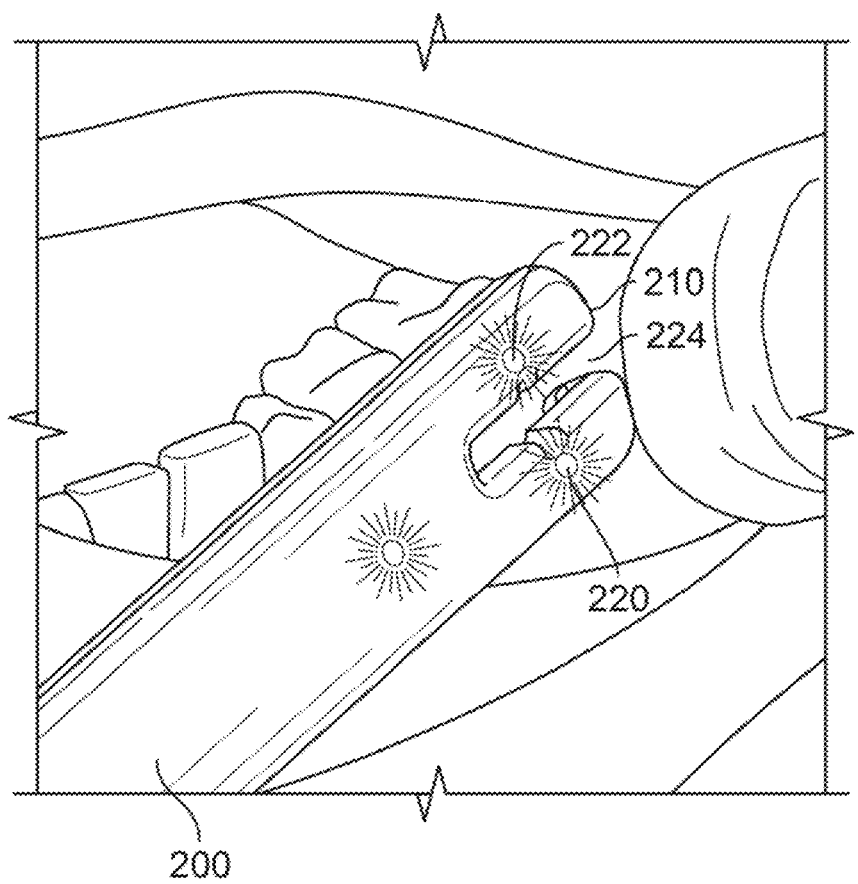
Figure 31:
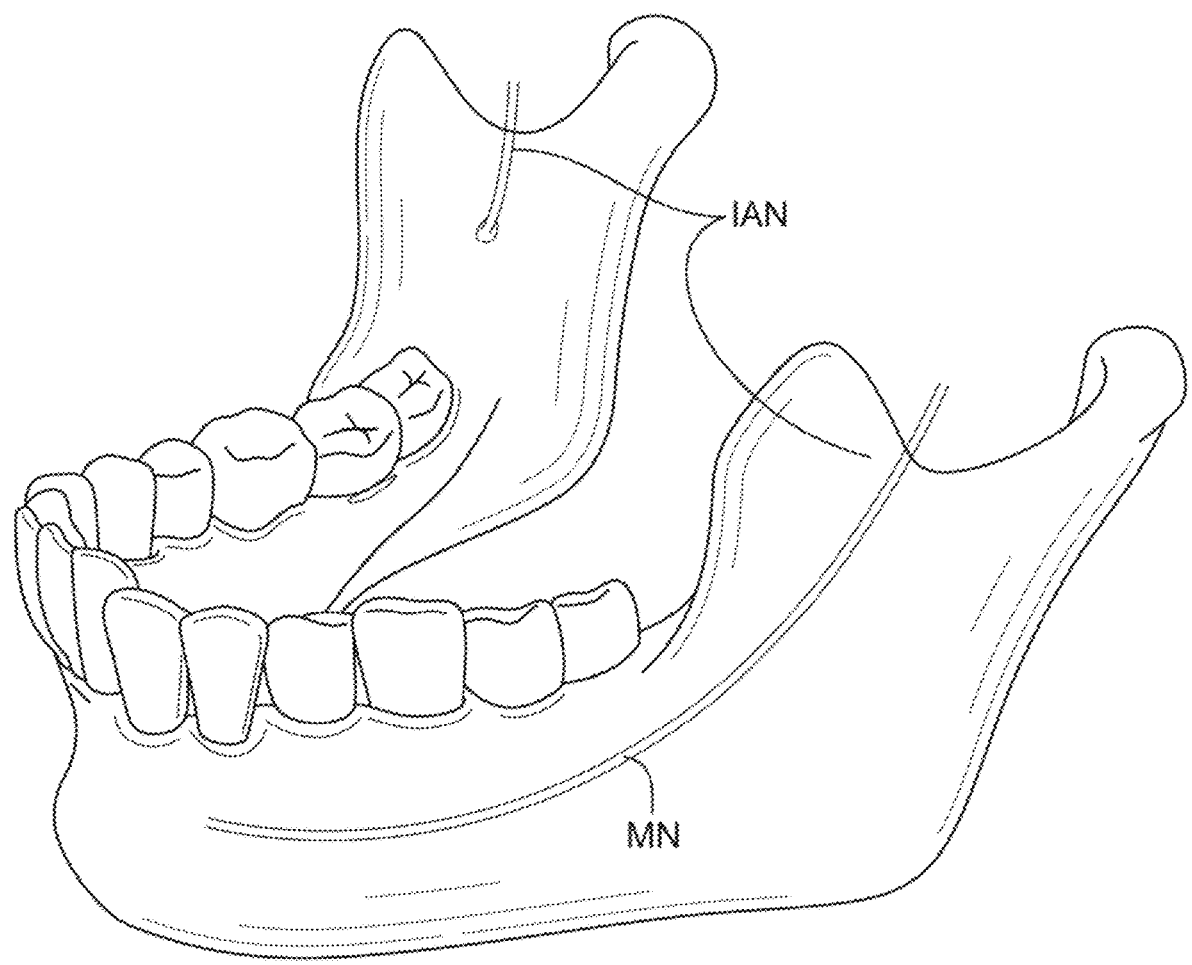

This procedure is shown in FIGS. 29 and 30. As shown at the starting point of FIG. 29, the dental use device 200 is positioned within a patient's open mouth such that the bottom surface (not shown in FIG. 29) gently contacts the skin or hovers just slightly above it in the area of the molars as near to the mental nerve MN as possible. In this way the target blood vessel at the MN will generally be perpendicular to the centerline CL of the dental use device 200. The dental use device 200 is then moved toward the general area of the target blood vessel, in the direction of Arrow C. With the dental use device 200 turned on, the sensors will begin to serially sense backscattered infrared light bouncing off the skin.

As the dental use device 200 is moved toward the position shown in FIG. 30, and now with the vessel associated with the MN positioned within the circular portion 225 of slotted aperture 224, LEDs 220, 222 will illuminate. In certain embodiments of the invention, the CPU can be calibrated such that the LEDs 220, 222 illuminate with greater intensity the closer the vessel is to being within the circular portion 225 of slotted aperture 224. In other embodiments, and in the preferred embodiment, the LEDs are simply on/off as it can be difficult in certain lighting to ascertain variable LED intensities. Either way, the LED indicators may also be supplemented with audible notes, if desired.

Once the target blood vessel is positioned within the circular portion 225 of slotted aperture 224, the caretaker will keep the device still and insert a hypodermic needle through the circular portion 225 of slotted aperture 224 and into the MN. As discussed above, the caretaker may also locate the hypodermic needle against the patient's skin inside the mouth and withdraw the device 200 by sliding the device such that the hypodermic needle travels through the slot 224. Each of the devices 100, 200 may also include additional LED lights (not shown) on or about the bottom surface, such as mounted on bottom surface 134 of device 100 or bottom surface 234 of device 200. Preferably the LED lights will be mounted toward the distal end, 110, 210, respectively, such that the lights can illuminate the area of interest of the patient's skin. Those LED lights can be "always on," or can illuminate only when the LEDs 120, 122, 220, 222 are illuminated. The LED lights can also have their own on/off switch which operates independent of the on/off buttons 114, 214.

While not shown, it will be appreciated that in preferred embodiments four LED lights can be mounted between the infrared light emitters 142a, 142b, 142c, or 242a, 242b, 242c, respectively, and three infrared light receivers 144a, 144b, 144c, or 244a, 244b, 244c, respectively. In that case, two LEDs will be aligned along each column C1, C2 and between rows R1, R2, and R2, R3. Other numbers and locations of LEDs are also possible.

It is also possible that the LED lights can be illuminated as the device approaches a blood vessel. That is, when a pair of sensor/receivers is receiving a reduced backscatter signal as compared to a prior reading an adjacent LED light may illuminate. This provides a visual indication to the caretaker that (s)he is approaching a blood vessel and moving the device in a proper direction.

To keep either device sanitary, a caretaker may apply a mylar tape (not shown) over portions of the device contacting a patient. In this regard, it has been found that a ½" wide roll of mylar tape may be perforated every 1", so that 1" long rectangular pieces may be readily applied to the devices. The mylar tape is preferably a dark blue color commonly used in the medical and dental industries as it has been found that this color is most compatible with infrared signals as it appears not to block any signal or otherwise cause degradation.

While the present invention has been described with reference to certain exemplary embodiments, it will be appreciated by those skilled in the art that various changes may be made and equivalents may be substituted for elements thereof without departing from the scope of the subject disclosure. In addition, modifications may be made to adapt a particular situation or material to the teachings of the subject disclosure without departing from the essential scope thereof.

It is to be understood, therefore, that the subject disclosure is not limited to the particular aspects disclosed, but it is intended to cover modifications within the spirit and scope of the exemplary embodiments described above.

We claim:
1. A vessel location assistance device comprising:
 a housing having a proximal portion and a distal portion, said proximal portion and said distal portion spaced apart along a centerline of said housing, said housing having a top portion and a bottom portion;

an aperture positioned in said distal portion along said centerline, said aperture penetrating through said top portion and said bottom portion of said housing;

at least one light associated with said housing;

three infrared light emitters adapted to emit infrared light from said bottom portion of said housing to a patient and three infrared light receivers adapted to receive backscattered infrared light reflected from the patient;

said three infrared light emitters and said three infrared light receivers arranged in pairs along equally spaced rows, including a middle row and two remaining rows, each equally spaced row extending perpendicular to said centerline, wherein said middle row of said three rows is aligned with said aperture;

said three emitters and three receivers arranged in two columns extending along axes equally spaced and parallel to said centerline;

wherein each pair of said three infrared light emitters and three infrared light receivers is serially and repeatedly energized to emit infrared light and detect backscattered infrared light intensity from said patient when said housing is positioned on a patient's skin, each of said detection intensities being converted to a voltage;

wherein, when a voltage of said middle row is less than a voltage of each of said two remaining rows said at least one light illuminates to provide an indication of the presence of a patient's blood vessel nearest said middle row of said three rows;

the device further comprising a central processing unit, said central processing unit being programmable to adjust a divergence level between said voltage of said middle row and said voltage of each of the two remaining rows prior to said one light illuminating to indicate the presence of a patient's blood vessel nearest said middle row of said three rows.

2. The vessel location assistance device of claim 1, wherein said infrared light emitters are arranged along a single column.

3. The vessel location assistance device of claim 1, wherein said light is a pair of lights aligned with said middle row of said three rows.

4. The vessel location assistance device of claim 1, further comprising a pair of wings extending parallel to said bottom portion, each of said wings having an open slot extending perpendicular to said centerline and along an axis of said middle row.

5. The vessel location assistance device of claim 4, wherein said open slots are V-shaped.

6. The vessel location assistance device of claim 1, wherein said proximal portion and said distal portion of said housing are separable.

7. The vessel location assistance device of claim 6, wherein said distal portion is sized and configured to fit within a patient's mouth such that said middle row can reach at least to the inferior alveolar nerve adjacent to and on the medial side of the ramus of the mandible.

8. The vessel location assistance device of claim 6, further comprising a central processing unit and a battery, said central processing unit and said battery being located within said proximal portion of said device.

9. The vessel location assistance device of claim 8, wherein said three infrared light emitters and said three infrared light receivers are located within said distal portion of said device.

10. The vessel location assistance device of claim 5, further comprising a plastic covering protecting said distal end of said device from bodily fluids.

11. The vessel location assistance device of claim 1, wherein said light is a blue light emitting diode (LED) light.

12. The vessel location assistance device of claim 1, wherein said light is a red light emitting diode (LED) light.

13. The vessel location assistance device of claim 1, wherein said three infrared light receivers are spaced apart to avoid crosstalk.

14. The vessel location assistance device of claim 1, wherein said aperture is a circle, oval, rectangle, or slot sized to permit penetration by a hypodermic needle.

15. The vessel location assistance device of claim 1, wherein a minimum level of backscattered infrared light is required in all three infrared light receivers prior to said at least one light illuminating.

16. The vessel location assistance device of claim 1, wherein each pair of said three emitters and three receivers is serially energized.

17. The vessel location assistance device of claim 1, wherein each pair of said three emitters and three receivers is serially energized, repeating at a rate between 4 and 6 times per second.

18. The vessel location assistance device of claim 1, wherein said at least one light includes an intensity, wherein said intensity is adjustable.

19. The device of claim 18, wherein said indication is additionally by audial means.

20. The vessel location assistance device of claim 1, further comprising indentations on an exterior of said housing between said top portion and said bottom portion adjacent said aperture.

21. The vessel location assistance device of claim 20, wherein said indentations are V-shaped.

22. The vessel location assistance device of claim 1, wherein nearest said middle row of said three rows is below said middle row of said three rows.

23. A vessel location assistance device comprising:

a housing having a proximal portion and a distal portion, said proximal portion and said distal portion spaced apart along a centerline of said housing, said housing having a top portion and a bottom portion;

an aperture positioned in said distal portion along said centerline, said aperture penetrating through said top portion and said bottom portion of said housing;

at least one light associated with said housing;

three infrared light emitters adapted to emit infrared light from said bottom portion of said housing to a patient and three infrared light receivers adapted to receive backscattered infrared light reflected from the patient;

said three infrared light emitters and said three infrared light receivers arranged in pairs along equally spaced rows, including a middle row and two remaining rows, each equally spaced row extending perpendicular to said centerline, wherein said middle row of said three rows is aligned with said aperture;

said three emitters and three receivers arranged in two columns extending along axes equally spaced and parallel to said centerline;

wherein each pair of said three infrared light emitters and three infrared light receivers is serially and repeatedly energized to emit infrared light and detect backscattered infrared light intensity from said patient when said housing is positioned on a patient's skin, each of said detection intensities being converted to a voltage;

wherein, when a voltage of said middle row is less than a voltage of each of said two remaining rows said at least one light illuminates to provide an indication of the presence of a patient's blood vessel nearest said middle row of said three rows;

wherein a divergence level between said voltage of said middle row and said voltage of each of said two remaining rows is user adjustable between at least two settings via either a rheostat or a central processing unit.

24. The vessel location assistance device of claim 23, wherein said adjustment accounts for differing skin characteristics.

25. The vessel location assistance device of claim 24, wherein said differing skin characteristics is the amount of subcutaneous fatty tissue a patient has or skin tone.

26. The vessel location assistance device of claim 14, wherein nearest said middle row of said three rows is below said middle row of said three rows.

27. A vessel location assistance device comprising:

a housing having a proximal portion and a distal portion, said proximal portion and said distal portion spaced apart along a centerline of said housing, said housing having a top portion and a bottom portion;

three infrared light emitters adapted to emit infrared light from said bottom portion of said housing to a patient and three infrared light receivers adapted to receive backscattered infrared light reflected from the patient;

said three infrared light emitters and said three infrared light receivers arranged in pairs along equally spaced rows, including a middle row and two remaining rows, each equally spaced row extending perpendicular to said centerline;

said three emitters and three receivers arranged in two columns extending along axes equally spaced and parallel to said centerline;

wherein each pair of said three infrared light emitters and three infrared light receivers is serially and repeatedly energized to emit infrared light and detect backscattered infrared light intensity from said patient when said housing is positioned on a patient's skin, each of said detection intensities being converted to a voltage;

wherein, when a voltage of said middle row is less than a voltage of each of said two remaining rows said device indicates the presence of a patient's blood vessel nearest said middle row of said three rows;

the device further comprising a central processing unit, said central processing unit being programmable to adjust a divergence level between said voltage of said middle row and said voltage of each of the two remaining rows prior to indicating the presence of a patient's blood vessel nearest said middle row of said three rows.

28. The vessel location assistance device of claim 21, further comprising a plastic covering protecting said device from bodily fluids.

29. The vessel location assistance device of claim 21, wherein nearest said middle row of said three rows is below said middle row of said three rows.

* * * * *